(12) United States Patent
Ramasamy et al.

(10) Patent No.: US 11,686,729 B2
(45) Date of Patent: Jun. 27, 2023

(54) BACTERIOPHAGE-BASED ELECTROCHEMICAL BACTERIAL SENSORS, SYSTEMS, AND METHODS

(71) Applicant: University of Georgia Research Foundation, Inc., Athens, GA (US)

(72) Inventors: Ramaraja P. Ramasamy, Watkinsville, GA (US); Yan Zhou, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 929 days.

(21) Appl. No.: 16/464,645

(22) PCT Filed: Nov. 29, 2017

(86) PCT No.: PCT/US2017/063605
§ 371 (c)(1),
(2) Date: May 28, 2019

(87) PCT Pub. No.: WO2018/102350
PCT Pub. Date: Jun. 7, 2018

(65) Prior Publication Data
US 2020/0033340 A1 Jan. 30, 2020

Related U.S. Application Data

(60) Provisional application No. 62/427,377, filed on Nov. 29, 2016.

(51) Int. Cl.
*G01N 33/569* (2006.01)
*G01N 33/50* (2006.01)
*C12N 7/00* (2006.01)
*G01N 33/543* (2006.01)
*G01N 33/554* (2006.01)

(52) U.S. Cl.
CPC ......... *G01N 33/56911* (2013.01); *C12N 7/00* (2013.01); *G01N 33/5438* (2013.01); *G01N 33/54326* (2013.01); *G01N 33/554* (2013.01); *C12N 2795/10131* (2013.01); *G01N 2333/005* (2013.01)

(58) Field of Classification Search
None
See application file for complete search history.

(56) References Cited

U.S. PATENT DOCUMENTS

2009/0155768 A1 6/2009 Scholl

OTHER PUBLICATIONS

Suresh et al., Analyst, 2012, 137, 4086-4092. (Year: 2012).*
Viswanathan et al., Biosensors and Bioelectronics, 2009, 24:1984-1989. (Year: 2009).*
Privett et al., Anal. Chem., 2010, 82:4723-4741. (Year: 2010).*
Simon, Proc. Nat. Acad. Sci. USA, 1972, 69(4):907-911). (Year: 1972).*
Morita et al., FEMS Microbiology Letters, 2002, 211(1):77-83. (Year: 2002).*
Hurley et al., Avian Diseases, 2008, 52:599-607. (Year: 2008).*
Guenther et al., Bacteriophage, 2011, 1(2): 94-100. (Year: 2011).*
Gervais et al., Sensors and Actuators B, 2007, 125:615-621. (Year: 2007).*
Yan Zhou and Ramaraja P. Ramasamy, "Phase-based Electrochemical Biosensors for Detection of Pathogenic Bacteria", 2015 Meet. Abstr. MA2015-02 1822.
Chen et al., "Bacteriophage-based nanoprobes for rapid bacteria separation", Nanoscale, 2015, pp. 16230-16236, vol. 7, The Royal Society of Chemistry.
Fratamico et al., "Rapid isolation of *Escherichia coli* 0157:H7 from enrichment cultures of foods using an immunomagnetic separation method", Food Microbiology, 1992, pp. 105-113, vol. 9, Academic Press Limited.
Jin et al., "Efficient bacterial capture with amino acid modified magnetic nanoparticles", Water Research, 2014, pp. 124-134, vol. 50, Elsevier Ltd.
Kanayeva et al., "Efficient Separation and Sensitive Detection of Listeria monocytogenes Using an Impedance Immunosensor Based onMagnetic Nanoparticles, a Microfluidic Chip, and an Interdigitated Microelectrode", Journal of Food Protection, 2012, pp. 1951-1959, vol. 75, No. 11, International Association for Food Protection.
Oravcovà et al., "Limitation in the detection of Listeria monocytogenes in food in the presence of competing Listeria innocua", Journal of Applied Microbiology, 2008, pp. 429-437, vol. 104, The Society for Applied Microbiology.
Shan et al., "Immunomagnetic nanobeads based on a streptavidin-biotin system for the highly efficient and specific separation of Listeria monocytogenes", Food Control, 2014, pp. 138-142, vol. 45, Elsevier Ltd.
Singh et al., "Bacteriophage based probes for pathogen detection", Analyst, 2012, pp. 3405-3421, vol. 137, The Royal Society of Chemistry.
Stevens et al., "Bacterial Separation and Concentration from Complex Sample Matrices: A Review", Critical Reviews in Microbiology, 2004, pp. 7-24, vol. 30, No. 1, doi: 10.1080/10408410490266410.
Wadud et al., "Evaluation of immunomagnetic separation in combination with ALOA Listeria chromogenic agar for the isolation and identification of Listeria monocytogenes in ready-to-eat foods", Journal of Microbiological Methods, 2010, pp. 153-159, vol. 81, Elsevier Ltd.
Wang et al., "Development of a novel bacteriophage based biomagnetic separation method as an aid for sensitive detection of viable *Escherichia coli*", Analyst, 2016, pp. 1009-1016, vol. 141, The Royal Society of Chemistry.

(Continued)

*Primary Examiner* — Nicole Kinsey White
(74) *Attorney, Agent, or Firm* — Thomas Horstemeyer, LLP

(57) ABSTRACT

The present disclosure includes methods and systems of detecting bacteria in a sample using phage-functionalized sensors, methods of enriching a sample with phage-functionalized magnetic particles, phage-functionalized magnetic particles and methods of making phage-functionalized magnetic particles.

22 Claims, 17 Drawing Sheets

(56) References Cited

OTHER PUBLICATIONS

Xiong et al., "Development of an immunomagnetic separation method for efficient enrichment of *Escherichia coli* O157:H7", Food Control, 2014, pp. 41-45, vol. 27, Elsevier Ltd.

Yang et al., "Rapid detection of Listeria monocytogenes by nanoparticle-based immunomagnetic separation and real-time PCR", International Journal of Food Microbiology, 2007, pp. 132-138, vol. 118, Elsevier Ltd.

Zhan et al., "Efficient removal of pathogenic bacteria and viruses by multifunctional amine-modified magnetic nanoparticles", Journal of Hazardous Materials, 2014, pp. 115-123, vol. 124, Elsevier Ltd.

Shaban I et al. "Magnetically-assisted impedimetric detection of bacteria using phage-modified carbon microarrays," Talanta, Aug. 13, 2013 (Aug. 13, 2013), vol. 116, pp. 1047-1053.

Zhou et al. "Phage-based electrochemical biosensors for detection of pathogenic bacteria" ECS Trans. Oct. 11, 2015 (Oct. 11, 2015), vol. 69, No. 38, pp. 1-8.

Muzard et al. "M13 bacteriophage-activated superparamagnetic beads for affinity separation," Small, May 23, 2012 (May 23, 2012), vol. 8, No. 15, Pgd. 2403-2411.

Yang et al. "Virus electrodes for universal biodetection," Anal Chem. May 15, 2006 (May 15, 2006), vol. 78, No. 10, pp. 3265-3270.

Tolba et al. "Oriented immobilization of bacteriophages for biosensor applications," Appl Environ Microbial. Nov. 30, 2009 (Nov. 30, 2009), vol. 76, No. 2, pp. 528-535. entire document.

Garcia-Aljaro et al. "Carbon nanotubes-based chemiresistive biosensors for detection of microorganisms," Biosens Bioelectron, Jul. 30, 2010 (Jul. 30, 2010), vol. 26, No. 4, pp. 1437-1441.

Baccar et al. "Multi-wall carbon nanotubes deposited on gold electrode for bacteria detection," Journal of Surfaces and Interfaces of Materials, Mar. 1, 2013 (Mar. 1, 2013), vol. 1, pp. 56-59.

Zhou et al. "Charge-Directed Immobilization of Bacteriophage on Nanostructured Electrode for Whole-Cell Electrochemical Biosensors," Anal Chem. May 22, 2017 (May 22, 2017), vol. 89, No. 11, pp. 5734-5741.

* cited by examiner

FIG. 5A
FIG. 5B
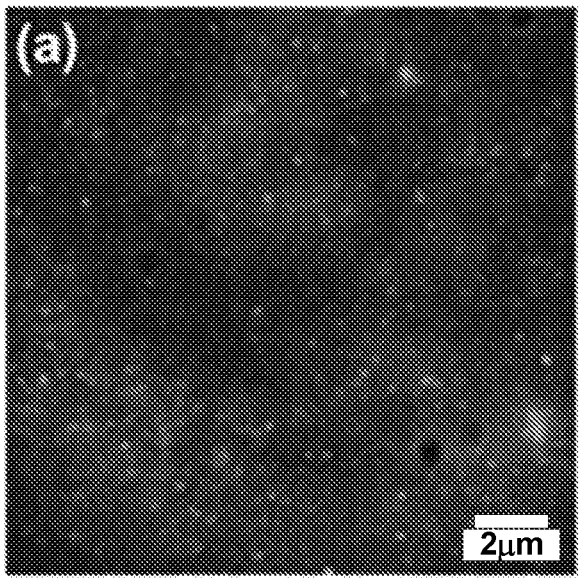
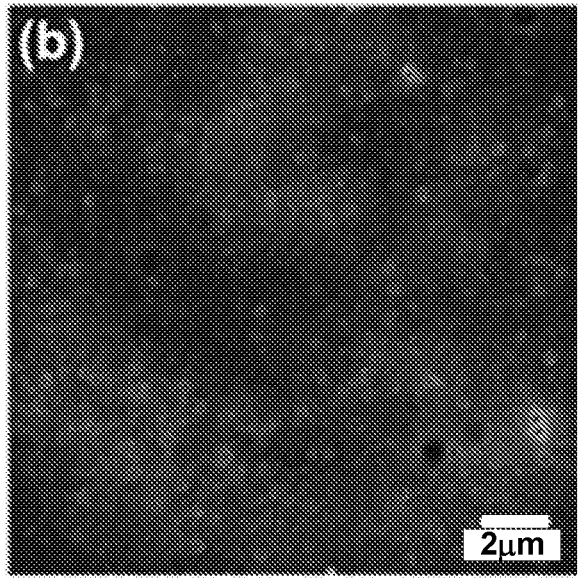
FIG. 5C
FIG. 5D
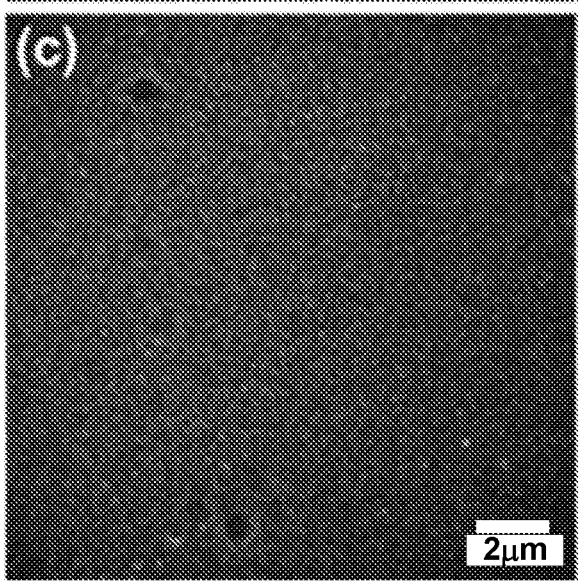
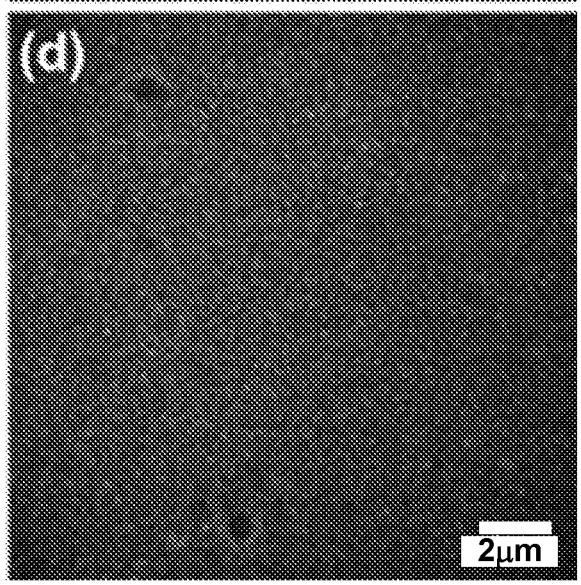

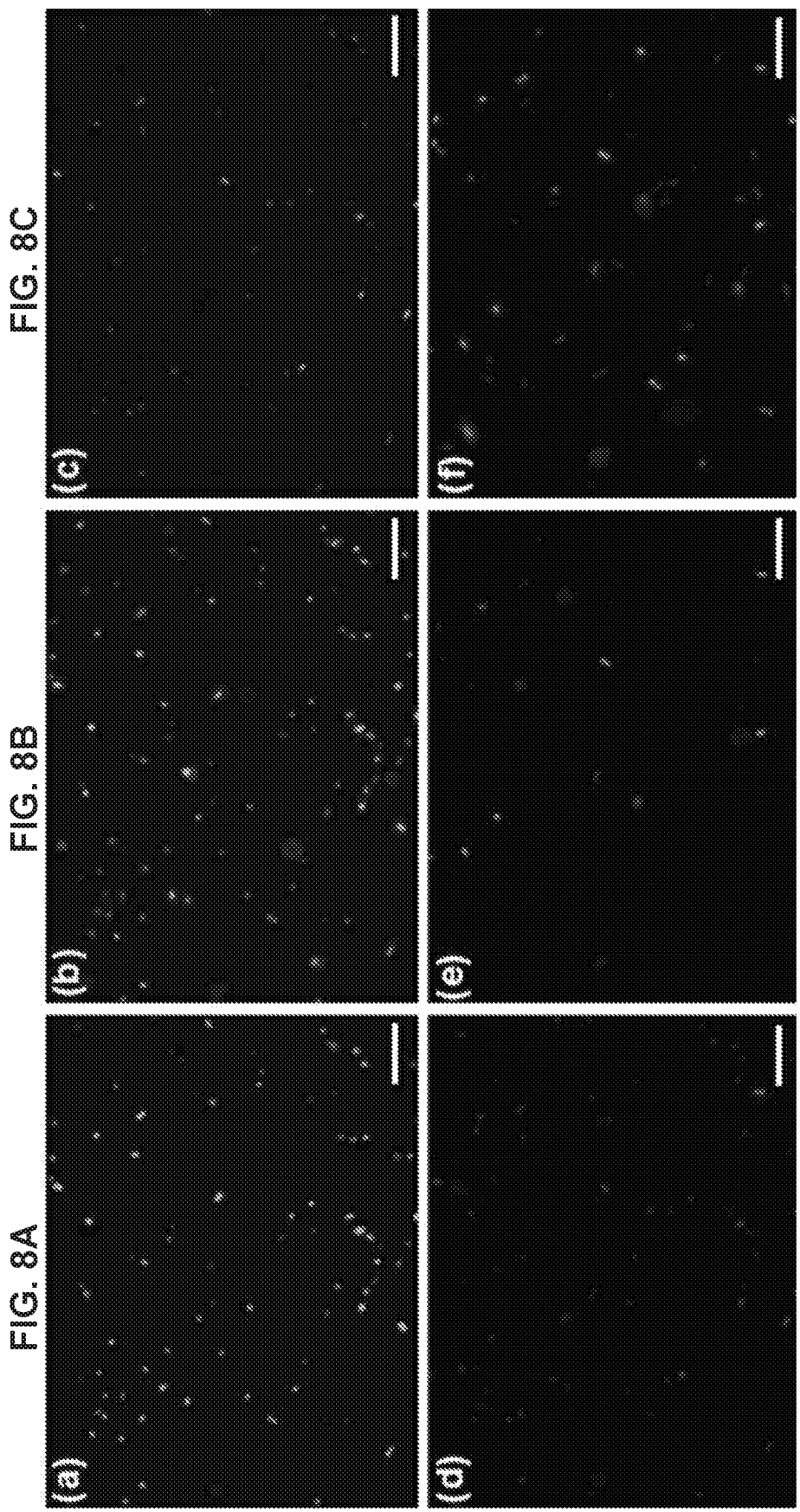

BACTERIOPHAGE-BASED ELECTROCHEMICAL BACTERIAL SENSORS, SYSTEMS, AND METHODS

CROSS-REFERENCE TO RELATED APPLICATIONS

This application is the 35 U.S.C. § 371 national stage of PCT application having serial number PCT/US17/63605, filed on Nov. 29, 2017. This application also claims priority to U.S. provisional application entitled "BACTERIOPHAGE-BASED ELECTROCHEMICAL BACTERIAL SENSORS, SYSTEMS, AND METHODS," having Ser. No. 62/427,377 filed on Nov. 29, 2016, which are entirely incorporated herein by reference.

STATEMENT REGARDING FEDERALLY SPONSORED RESEARCH OR DEVELOPMENT

This invention was made with Government support under Grant No. CBET-1637863 awarded by the National Science Foundation. The Government has certain rights in this invention.

BACKGROUND

Bacterial pathogens are universally present in the environment and can easily contaminate food or water to cause serious food-borne illness to humans. Centers for disease control and prevention (CDC) estimates that one in six Americans get sick from contaminated food or beverages, 128,000 are hospitalized and 3000 die each year in the United States. Foods that sickened people were contaminated with pathogenic bacteria or toxins. In 2015, 11 cases of food-borne outbreaks were investigated on pathogens including *Salmonella* spp., *E. coli* O157, and *Listeria monocytogenes*. The prevention of such outbreaks of food-borne diseases is critical and requires an accurate and sensitive detection of contaminations before distribution in the market.

Bacterial pathogens are important targets for detection and identification in various applications, such as food safety, environmental pollution, and public health. Conventional methods for bacterial identification include standard microbiology or biochemical procedures, such as culture and cell counting of bacteria, enzyme linked immunosorbent assay (ELISA), polymerase chain reaction (PCR), flow cytometry, etc. While being highly reliable, these methods are also laborious, time-consuming, typically expensive, and require special laboratory environments to avoid contamination, making them unsuitable for rapid screening purposes by an unskilled user outside the laboratory set up.

SUMMARY

Embodiments of the present disclosure include a method of detecting bacteria in a sample, including the steps of: a) providing magnetic particles functionalized with a first plurality of bacteriophages specific for a target strain of bacteria to be detected. The bacteriophages are immobilized to the magnetic particle such that a majority of the phages are oriented in a head-in configuration relative to the magnetic particle such that a head of the bacteriophage can be coupled to the magnetic particle: contacting the phage-functionalized magnetic particles with a sample contaminated with the target bacteria, such that the bacteriophages bind to bacterial cells of the target strain in the sample thereby coupling the bacterial cells to the phage-functionalized magnetic particles; b) applying a magnetic field to the sample to separate the magnetic particle-coupled bacterial cells from other components in the sample to provide an enriched sample comprising a greater concentration of the target bacteria than the original sample; c) contacting the enriched sample with a bacteriophage-modified electrode. The electrode can include an electrode material, a layer of multi-walled, carbon nanotubes (MWCNTs) on a surface of the electrode material, and a second plurality of bacteriophages specific for the target strain of bacteria, wherein the majority of the phages on the electrode are oriented in a head-in, tail-out configuration relative to the electrode surface such that a head of the bacteriophage is coupled to the multi-walled, carbon nanotubes, wherein the second plurality of bacteriophages are capable of binding the target bacteria in the enriched sample; and d) applying an electrical signal to the bacteriophage-modified electrode such that binding of the target bacteria to the phage-modified electrode produces a detectable impedimetric signal.

Embodiments of the present disclosure also include a system for detecting bacteria in a sample, including a) magnetic particles functionalized with bacteriophages specific for a target strain of bacteria to be detected. The bacteriophages can be immobilized to the magnetic particle such that a majority of the phage are oriented in a head-in configuration relative to the magnetic particle such that a head of the bacteriophage is coupled to the magnetic particle and the tail of the bacteriophage is free to recognize bacterial cells of the target strain in a sample containing the target bacteria, thereby coupling the bacterial cells to the phage-functionalized magnetic particles. Embodiments of the system also include: b) a magnet capable of providing a magnetic field to the sample to separate magnetic particle-coupled bacterial cells from other components in the sample to provide an enriched sample comprising a greater concentration of the target bacteria than the original sample; c) a bacteriophage-modified electrode including an electrode material, a layer of multi-walled, carbon nanotubes (MWCNTs) on a surface of the electrode material, and bacteriophages specific for the target strain of bacteria immobilized to the MWCNT's, wherein the majority of the phages on the electrode can be oriented in a head-in, tail-out configuration relative to the electrode surface such that a head of the bacteriophage is coupled to the multi-walled, carbon nanotubes, wherein the second plurality of bacteriophages are capable of binding the target bacteria in the enriched sample; and d) a three-electrode electrochemical cell, in which the bacteriophage-modified electrode is a working electrode. The cell can further include a counter electrode and a reference electrode in electrochemical communication with the working electrode, and a potentiostat to supply an electrical signal to the electrochemical cell. The potentiostat can monitor changes in electrochemical parameters of the working electrode, wherein binding of target bacteria to the phage-modified electrode produces a detectable impedimetric signal.

Embodiments of the present disclosure also include a method of making a system for detecting bacteria in a sample, including a) providing bacteriophages specific for a target strain of bacteria to be detected, where the bacteriophages include a head and a tail; b) immobilizing the bacteriophages to magnetic particles such that a majority of the phages are oriented in a head-in configuration relative to the magnetic particle, where the head of the bacteriophage is coupled to the magnetic particle; and c) preparing a bacteriophage-modified electrode. In embodiments, preparing the bacteriophage-modified electrode includes modifying a surface of an electrode to form a layer of multi-walled, carbon nanotubes (MWCNTs) on a surface of the electrode material, adding a positively charged charge modifying compound to the surface of the electrode to provide the electrode with a positive charge, applying a positive potential to the MWCNT modified electrode to provide a positive surface charge to the electrode, contacting the positively charged electrode with a composition comprising a second plurality of bacteriophages specific for the target strain of bacteria, such that the positive surface charge of the electrode facilitates coupling of the bacteriophages to the electrode surface in a head-in, tail-out configuration in manner where the second plurality of bacteriophages can bind to the target bacterial species in a sample.

Embodiments of the present disclosure include a method of enriching a sample, including: a) providing phage-functionalized magnetic particles to a sample wherein each magnetic particle is non-covalently coupled to at least one target-strain specific bacteriophage such that a majority of the phages are oriented in a head-in configuration relative to the magnetic particle such that a head of the bacteriophage is coupled to the magnetic particle; b) introducing the phage-functionalized magnetic particles to a sample containing the target bacteria, wherein the tail of the bacteriophage is free to attach to bacterial cells in the sample, thereby coupling the bacterial cells to the phage-functionalized magnetic particles; and c) providing a magnetic field to the sample to separate the magnetic particle-coupled bacterial cells from other components in the sample, thereby providing an enriched sample comprising a greater concentration of the target bacteria than the original sample.

Embodiments of the present disclosure also include a phage-functionalized particle including at least one bacteriophage and a magnetic particle, wherein the majority of bacteriophages can be non-covalently coupled to the magnetic particle in a head-in, tail-out configuration and wherein each magnetic particle can be coupled to at least one bacteriophage.

Embodiments of the present disclosure also include a method of making a phage-functionalized particle, including contacting at least one bacteriophage to a magnetic particle, such that the majority of bacteriophages couple to the magnetic particle in a head-in, tail-out configuration and wherein each magnetic particle is coupled to at least one bacteriophage, and wherein the coupling is via a non-covalent linkage.

Other compositions, apparatus, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A illustrates surface functionalization of the magnetic particle with phage(s) specific for (e.g., that specifically binds) a target bacterial cell, and FIG. 1B illustrates binding and magnetic separation of bacterial cells from a sample.

FIGS. 5A-5D illustrate fluorescent images of: (5A-B) surface immobilized phage particles by electric-field induced covalent attachment; (5C-D) surface immobilized phage by covalent attachment without electric-field induced attachment. Red marks (dots in FIG. 5B) indicate surface immobilized phages. 140 phage particles were detected in 5B, and 9 were detected in 5D using the method described above. The laser intensity used was 114 W/cm$^2$.

(FIG. 6A) Lysis rings (pointed with arrows) were formed around the ITO electrode with immobilized phages; (FIG. 6B) No plaque was formed around the ITO electrode without surface immobilized phages.

FIGS. 8A-8F are representative images of bacterial cell lysis monitored by fluorescence microscope using the Backlight bacteria viability kit. (A) 10 min; (B) 15 min; (C) 20 min; (D) 25 min; (E) 30 min; (F) 35 min. Green dots (dots n FIGS. 8A-8C) represent live bacteria, and red dots (dots in FIGS. 8D-8F) represent lysed bacteria. The scale bar is 10 µm.

DETAILED DESCRIPTION

Figure 1A:
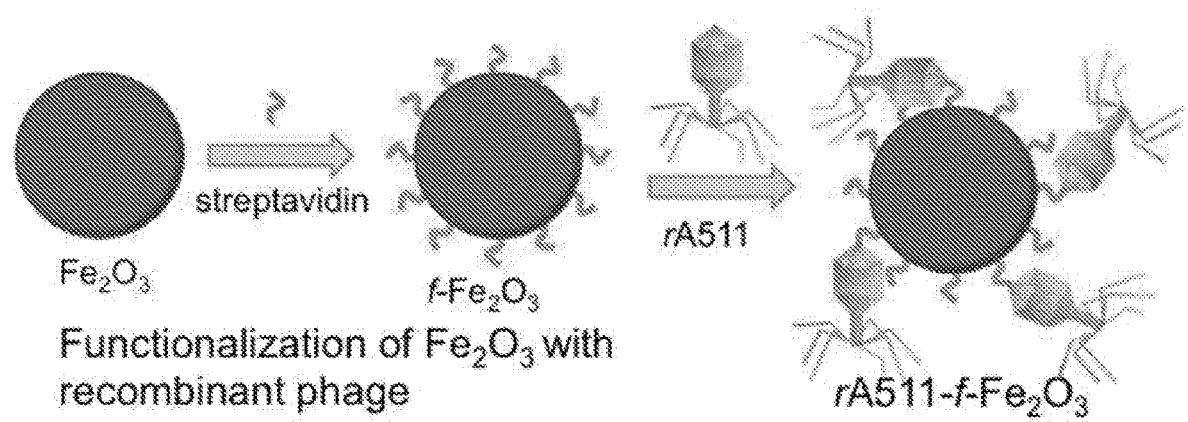
FIGS. 1A-1B illustrate schematic drawings of the methodology for magnetic separation of bacterial cells from a sample using phage functionalized magnetic nanoparticles.
Figure 1B:
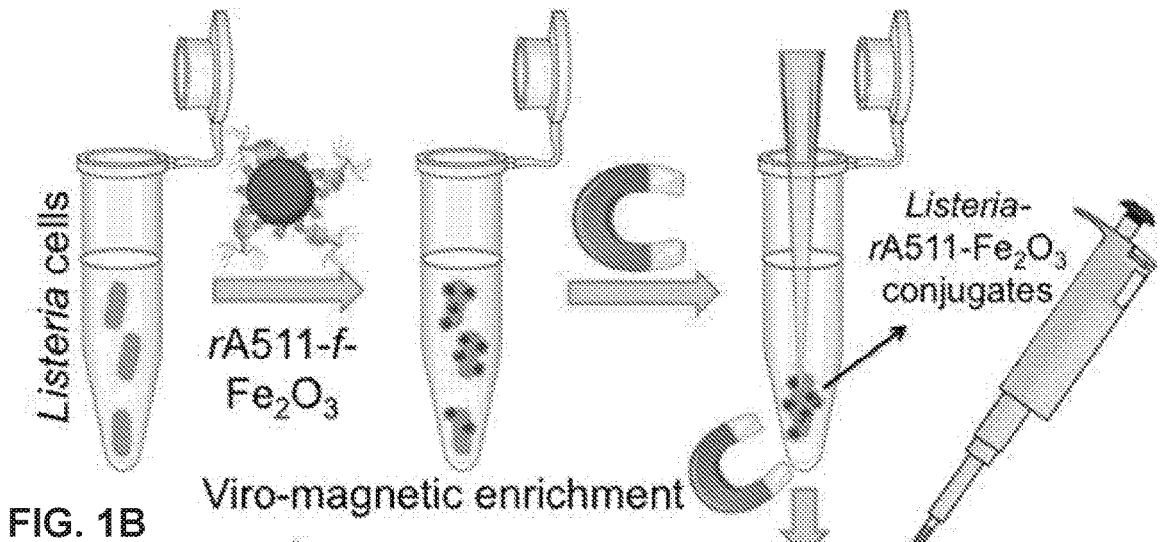
Figure 1C:
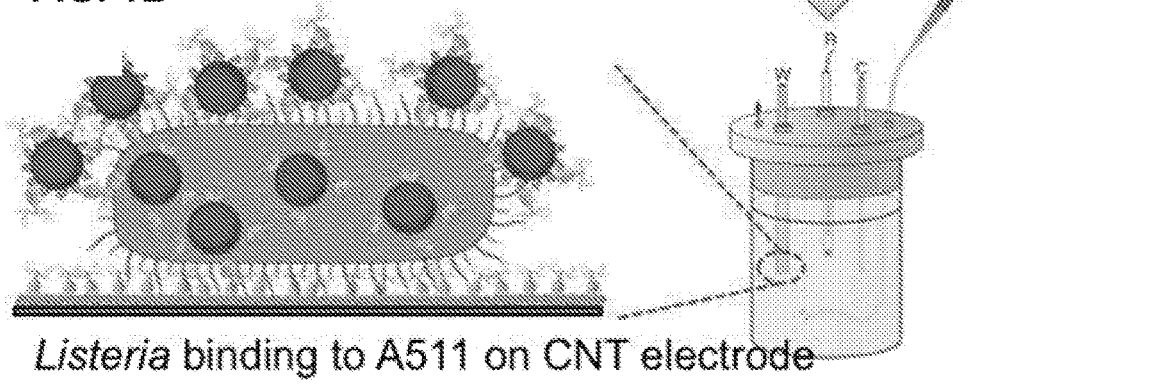
FIG. 1C illustrates bacterial cell detection using the phage modified electrode of the present disclosure.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification that are incorporated by reference, as noted in the application, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, organic chemistry, biochemistry, virology, electrochemistry, and the like, which are within the skill of the art. Such techniques are explained fully in the literature.

It must be noted that, as used in the specification and the appended embodiments, the singular forms "a," "an," and "the" include plural referents unless the context clearly dictates otherwise. Thus, for example, reference to "a support" includes a plurality of supports. In this specification and in the embodiments that follow, reference will be made to a number of terms that shall be defined to have the following meanings unless a contrary intention is apparent.

As used herein, the following terms have the meanings ascribed to them unless specified otherwise. In this disclosure, "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing the disclosed subject matter, the following terminology will be used in accordance with the definitions set forth below.

As used herein, "about," "approximately," and the like, when used in connection with a numerical variable, generally refers to the value of the variable and to all values of the variable that are within the experimental error (e.g., within the 95% confidence interval for the mean) or within +/−10% of the indicated value, whichever is greater.

As used herein, "isolated" indicates removed or separated from the native environment. An isolated virus, bacterial cell, peptide, protein (e.g., an enzyme), or other biological compound indicates the virus, cell, peptide, etc. is separated from its natural environment. Isolated virus particles, cells, peptides, etc., are not necessarily purified.

The term "polypeptides" and "protein" include proteins, such as enzymes, and fragments thereof. Polypeptides are disclosed herein as amino acid residue sequences. Those sequences are written left to right in the direction from the amino to the carboxyl terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

As used herein "functional variant" refers to a variant of a protein or polypeptide (e.g., a variant of a plant enzyme) that can perform the same functions or activities as the original protein or polypeptide, although not necessarily at the same level (e.g., the variant may have enhanced, reduced or changed functionality, so long as it retains the basic function).

"Identity," as known in the art, is a relationship between two or more polypeptide sequences, as determined by comparing the sequences. In the art, "identity" also refers to the degree of sequence relatedness between polypeptides as determined by the match between strings of such sequences. "Identity" and "similarity" can be readily calculated by known methods, including, but not limited to, those described in Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carilio, H., and Lipman, D., SIAM J Applied Math., 48: 1073 (1988).

The terms "native," "wild type", or "unmodified" in reference to an organism (e.g., plant or cell), polypeptide, protein or enzyme, are used herein to provide a reference point for a variant/mutant of an organism, polypeptide, protein, or enzyme prior to its mutation and/or modification (whether the mutation and/or modification occurred naturally or by human design). Typically, the unmodified, native, or wild type organism, polypeptide, protein, or enzyme has an amino acid sequence that corresponds substantially or completely to the amino acid sequence of the polypeptide, protein, or enzyme as it generally occurs naturally.

As used in the present disclosure, two materials are in "electrochemical communication" when electrons generated by a chemical reaction of one material (e.g., analyte or chemical substance of interest) can be transferred to and/or accepted by the other material (e.g., another chemical compound, a transducer material, and/or an electrode) or vice versa.

As used in the present disclosure, a "transducer" or "transducer material" describes a material capable of acting as an electronic transducer to transfer/deliver electrons from one material/reaction to another. For instance, in embodiments of the electrochemical sensors of the present disclosure, a sensor may include a transducer (e.g., a nanomaterial transducer) that is in electrical communication between a phage/bacterial cell and the electrode. In embodiments, the electrode is formed from and/or functionalized with a transducer material and/or enzymes may be directly or indirectly associated with the transducer material (e.g., by immobilization on the nanomaterial transducer).

The term "detectable" refers to the ability to perceive or distinguish a signal over a background signal. "Detecting" refers to the act of determining the presence of and recognizing a target or the occurrence of an event by perceiving a signal that indicates the presence of a target or occurrence of an event, where the signal is capable of being perceived over a background signal.

As used herein, the term "phage coupling ratio" is a measure of the number of phages coupled to a particular magnetic particle compared to the initial phage numbers. For example, 6 out of 10 phages were coupled with magnetic particles, the phage coupling ratio could be expressed as 0.6. In other examples, the phage coupling ratio refers to the average number of phages coupled per magnetic particle in a sample compared to the initial number of phages.

As used herein, "size" of a particle refers to the average diameter of a particle.

As used in the present disclosure, the term 'capture efficiency' is a measure of the number of bacteria cells captured by a particular phage-functionalized magnetic particle compared to the initial bacteria cell number in the sample. For example, if 70 out of 100 bacteria cells were captured by the magnetic particles, the capture efficiency could be expressed as 70%.

Discussion

Embodiments of the present disclosure encompass methods and systems for enriching and electrochemically detecting bacterial pathogens present in a sample, such as a consumable product (e.g., food or beverage). Embodiments include methods of detecting bacterial pathogens present in a sample, including both enriching/concentrating any bacteria present in the sample and electrochemically detecting the binding of bacterial cells to a bacteriophage-modified electrode in an electrochemical sensor. Embodiments also include systems for enriching and detecting the bacterial pathogens, as well as methods of making the sensors.

Among the myriad of detection methods, biosensors offer a viable solution to rapid and cost-effective method of bacterial detection. Biosensors are devices that incorporate a biological recognition element with high specificity towards target analytes. A typical biosensor includes three components, bioreceptor (e.g., enzyme, protein, antibody, DNA, and/or viruses), a transducer element, and data processing unit. Typically, biosensors can be categorized by the type of bioreceptors, or by the mode of transduction element. The transduction mode could be optical, piezo-electric or electrochemical. Electrochemical biosensors are of particular interest because of their simplicity, fast response and high sensitivity. The specificity and cost of an electrochemical biosensor is highly dependent on the type of the bio-recognition element being used, such as enzymes, antibodies, DNA/RNA, aptamers, or bacteriophages. While aptamers, antibodies, and enzymes possess high selectivity, they are highly susceptible to damage or loss of activity in harsh environmental conditions often used for bacterial cell detection. DNA-based detection methods cannot distinguish viable cells from dead cells and require sample processing. On the other hand, bacteriophage (or simply "phage") viruses are inexpensive, ubiquitous in nature, and possess robust stability.

As a bio-recognition element, bacteriophages offer high selectivity towards their host bacteria and can also discriminate between viable and nonviable cells. A phage could recognize its host bacterium through the bacterial surface receptor, followed by binding onto the bacterial cell. After penetrating the bacterial cell, a phage injects its genetic material (DNA/RNA), which initiate protein synthesis, phage assembly, and replication inside the bacterium. This leads to bacterial cell lysis (breaking open) and the release of new virus particles. The mechanism reflects a recognition system in which phage particles specifically recognize and bind only to their host bacterial cells. Thus, bacteriophages represent useful tools for specific binding of bacteria (Arya et al., 2011; Edgar, et al., 2006).

The present disclosure provides an electrochemical biosensor using phage as a bio-recognition element for whole cell detection constructed by immobilizing phage particles on electrode surfaces. The use of nanostructured electrodes for phage immobilization further enhances the sensitivity of electrochemical detection. Towards this end, various approaches have been proposed to immobilize phage on electrochemical biosensor platforms, from a simple physisorption (physical attachment) to covalent crosslinking (Stevens, et al., 2004; Nanduri, et al., 2007; Shabani, et al., 2008; Singh, et al, 2009; and Pearson, et al., 2013). Much of the effort in the published literature has been focused on increasing the number of surface phage particles per unit area, in which the phage was randomly oriented on the surface for either amperometric-based electrochemical biosensors, or for surface plasmon resonance-based optical biosensor construction (see, e.g., Ahn, et al., 2014; Tolba, et al., 2010). Since 95% of phages isolated to date are tailed, and possess asymmetric shape, it is important to achieve the desired orientation of phages on the transducer surface to function effectively as a bio-recognition element (Hosseinidoust, et al., Gervais, et al., 2007). For Myoviridae phages, that contain a distinct head (capsid)-tail structure such as the T4 phage, it is important to orient the phage in a manner that the majority of the capture proteins (tail fiber) are exposed to target the host bacterial cells. However, a vast majority of the published literature on phage-based biosensors do not address this problem satisfactorily. Asymmetrical phage particles immobilized on biosensor surface without a preferred orientation generally exhibit low bacteria capture efficiency as shown by Hosseinidoust et al. (2011) for T4 towards the capture of *E. coli* cells. This underscores the importance of oriented immobilization of bacteriophage on electrode surface for biosensing purposes.

Some attempts reported in the literature for oriented immobilization were based on a recombinant engineering of phage capsid proteins such as biotinylation of phage head proteins which immobilize phage in capsid down—tails up fashion (Gervais, et al., 2007, Edgar, et. al, 2006). This approach is fascinating but can be labor-intensive. Some attempts have been made for oriented phage immobilization on surfaces without recombinant engineering using electrophoretic method (see; Anany, et al., 2011; Han, et al., 2015, Richter, et al., 2016). Most phages have net negative charge, with a negatively charged capsid (head) and positively charged tail fibers. This charge difference between the head and tail fibers of the phage could be utilized for immobilizing phage on electrode surface using electrostatic interaction and electrophoretic deposition. For example, H. Anany et al. proposed a method for the oriented immobilization of bacteriophage on positively charged cellulose membrane that attracts large number of phage particles to its surface due to their net negative charge. Han et al, proposed the capture of T7 bacteriophage on an indium tin oxide surface through electrophoresis for virus detection. The electrophoretic trapping of phage particles offers a simple method to achieve a controllable array of phages in the correct orientation. Richter et al. studied the behavior of phage upon aligned along the electric field and applied the phage-modified substrate for flow cytometry.

In the methods and systems of the present disclosure, a charge-directed orientated strategy for phage immobilization on carbon nanotube modified electrode surface is provided for electrochemical detection of bacterial cells. In embodiments, this approach is combined with a sample enrichment technique, explained in greater detail below, which also employs bacteriophage and couples them to magnetic particles (micro- or nanoparticles) for sample separation to increase detection. The examples below describe a novel T2 bacteriophage-assisted carbon nanotube-based impedimetric biosensor for *E. coli* detection, in which the T2 was immobilized via electric field-induced immobilization as a biological recognition molecule on cationic polymer functionalized multiwall carbon nanotube (CNT) based electrodes. T2 phage has an octahedral capsid of size of 65 nm and tail length of 100 nm. It contains negative charge on the capsids (heads) and is positively charged on the tail fibers. Using electric field-induced immobilization, T2 phages could be oriented on positive charge functionalized CNT to enable the chemical anchoring of phage to the electrode through covalent linkage. The resulting T2 phage-modified CNT electrodes were used as biosensors for the detection of *E. coli* B using electrochemical impedance spectroscopy as the detection technique.

The methods and systems described in greater detail below also provide a method of enriching bacterial cells present in a sample to increase sensitivity of detection using the phage-modified electrochemical sensors of the present disclosure. In some embodiments, the magnetic particles can be functionalized (modified) using non-covalent linkages to a bacteriophage. In embodiments, the same species/strain of phage can be used to functionalize (modify) the magnetic particles as was used to functionalize the electrochemical bacteria sensor. In some embodiments, although the same bacteriophage strain is used in the enrichment and detection parts of the system/method, the phage used to functionalize the magnetic particle may also be genetically modified to include an affinity tag to interact with a complementary linker on the surface of the magnetic particle. The two methods can be used alone or together. Greater details are described below.

Embodiments of the present disclosure provide methods of enriching a sample including providing phage-functionalized (phage-modified) magnetic particles to a sample. Each magnetic particle can be functionalized by coupling (e.g. via covalent (e.g., a chemical) linkage, or by a physical, non-covalent linkage) to one or more bacteriophages that are specific to a target strain of bacteria, and the majority of the heads of the bacteriophages are coupled to the magnetic particle. Because a majority of the tails of the bacteriophages on the phage-functionalized magnetic particles are not bound to the magnetic particles, they are free to attach to the target bacteria in the sample. This is referred to herein as a "head-in, tail-out configuration". In embodiments, using a physical linking method to couple the phage to the magnetic particle results in a high percentage of the phage (e.g., a majority of the coupled phage) being coupled to the magnetic particle in the head-in, tail-out configuration. Thus the bacterial cells are now bound/attached to the phage that is coupled to the phage-functionalized magnetic particles. A magnetic field can be applied to the sample to separate the magnetic particle-coupled bacterial cells from other components in the sample, thereby providing an enriched sample (e.g. where the concentration of the target bacteria is higher than that of the original sample). In embodiments, the size of the magnetic particle is selected to achieve an optimal coupling ratio for a specific target bacteriophage. In some embodiments a micro-particle or a nanoparticle can be advantageous, depending on the phage selected. In embodiments, the magnetic particle can be from about 50 nm to about 5 μm (e.g. 150 nm, 500 nm, or 1 μm). In various embodiments, the target strain of bacteria can be *Listeria monocytogenes* and the bacteriophage can be A511 phages, P100 phages, or genetically modified variations thereof.

Embodiments of the present disclosure provide for phage-functionalized particles including at least one bacteriophage and a magnetic particle. In embodiments, the majority of the bacteriophages can be non-covalently coupled to the magnetic particles in a head-in, tail-out (e.g. head toward the particle, tail away from the particle) configuration and each magnetic particle can be coupled to at least one bacteriophage. In embodiments, the size of the magnetic particle is selected to achieve an optimal coupling ratio for a specific target bacteriophage. In some embodiments a microparticle or a nanoparticle can be advantageous, depending on the phage selected. In embodiments, the magnetic particle can be from about 150 nm to about 1 μm (e.g. 150 nm, 500 nm, or 1 μm). In various embodiments, the target strain of bacteria can be *Listeria monocytogenes* and the bacteriophage can be A511 phages, P100 phages, or genetically modified variations thereof.

The present disclosure provides for methods of making phage-functionalized particles, including contacting bacteriophages to magnetic particles. In embodiments, the majority of the bacteriophages can be non-covalently coupled to the magnetic particles in a head-in, tail-out configuration, and each magnetic particle can be coupled to at least one bacteriophage. When the contacting occurs, the magnetic particles can be in a sterilized suspension, and the contacting can occur under stirring or rotation. In embodiments the magnetic particles can be amine functionalized. In embodiments, the size of the magnetic particle is selected to achieve an optimal coupling ratio for a specific target bacteriophage or an optimal number of phages coupled to each magnetic particle (e.g. greater than or equal to 1). In some embodiments, a microparticle or a nanoparticle can be advantageous, depending on the phage selected. In embodiments, the magnetic particle can be from about 150 nm to about 1 μm (e.g. 150 nm, 500 nm, or 1 μm). In various embodiments, the target strain of bacteria can be *Listeria monocytogenes* and the bacteriophage can be A511 phages, P100 phages, or genetically modified variations thereof.

Bacteriophage-Based Sensors and Systems and Methods of Making

Embodiments of the present disclosure include bacteriophage-based sensors for detecting bacterial cells in a sample of interest. Embodiments also include devices/systems for enriching a sample to concentrate the amount of bacterial cells present in the sample (e.g., separating target bacterial cells from at least some components of the sample). The present disclosure also provides systems for combined enrichment and detection of bacterial cells in a sample. In embodiments, the bacteria to be detected are pathogenic bacteria (e.g., bacteria that cause disease in a subject, such as a human). In embodiments, the sample to be tested is a consumable food product (e.g., food, beverage, flavoring, etc.).

Systems and devices for enriching a target bacteria in a sample of interest include magnetic particles (e.g., micro- and/or nanoparticles) functionalized with a plurality of bacteriophage specific for a target strain of bacteria to be detected. In embodiments, the plurality of bacteriophage are coupled to the surface of the magnetic particle. In embodiments, the magnetic particles are magnetic nanoparticles. In embodiments, the magnetic nanoparticles are super paramagnetic nanoparticles (SPMNP), such as, but not limited to, $Fe_2O_3$ SPMNP. Depending on the phage selected, in some embodiments the magnetic particles can be microparticles (e.g. about 1 μm).

The bacteriophages are selected based on specific binding to a target bacteria. For instance, some possible parings of various bacterial strains and bacteriophage are presented in the Table below. Other bacteria/phage parings are known to those of skill in the art.

| Bacteria | Strain | Bacteriophage | Phage morphology |
|---|---|---|---|
| *Salmonella* | S. typhimurium ATCC19585 | P22 | Podoviridae |
| | S. enterica Arizonae CDC346-86 | SP6, P22, ST104, ST64T | Podoviridae |
| *E. coli* O157 | ATCC 43888 | PP01 | Myoviridae |
| | P1432 | e11/2, e4/1c | Myoviridae |
| | NCTC 12900, ATCC 43895 | CEV1 | Myoviridae |
| | *E. coli* O157:H7 1266 | AR1 | Myoviridae |
| *Listeria monocytogenes* | WSLC 1001(ATCC19112), WSLC 2096 or WSLC 2321 | P100 | Myoviridae |
| | WSLC 3009 | A511 | Myoviridae |
| | WSLC 1001/1042 | P35, A006, A500 | Siphoviridae |
| | WSLC 1001/1042 | P35 | Siphoviridae |

The bacteriophages are coupled to the magnetic particle such that a majority of the phages are oriented in a head-in, tail-out configuration relative to the magnetic particle such that the head of the bacteriophage is coupled to the magnetic particle and the tail portion of the bacteriophage is free to bind to bacterial cells of the target bacterial strain in a sample containing the bacteria. An embodiment of this process is illustrated in FIG. 1A. In embodiments, the bacteriophages are coupled to the magnetic particle via chemical bonding (e.g., via a linking molecule). In embodiments, the bacteriophages are coupled to the magnetic particle via non-covalent linkages (e.g. through hydrophobic and electrostatic interactions).

In embodiments, the bacteriophages are modified (e.g., genetically or otherwise) to increase the amount of phage oriented in the head-in, tail-out configuration (e.g., modification such that the head of the bacteriophage includes an affinity tag on the phage capsid). In embodiments, the magnetic particles are functionalized with a corresponding linker on the surface of the particle, where the linker is specific for the affinity tag on the phage capsid, such that the bacteriophage specifically couples to the magnetic particle via the phage head in a head-in, tail-out configuration. In embodiments, the magnetic particle is functionalized with streptavidin and the bacteriophage are biotinylated for attachment to streptavidin-functionalized magnetic particles, such as illustrated in FIG. 1A.

Figure 2A:
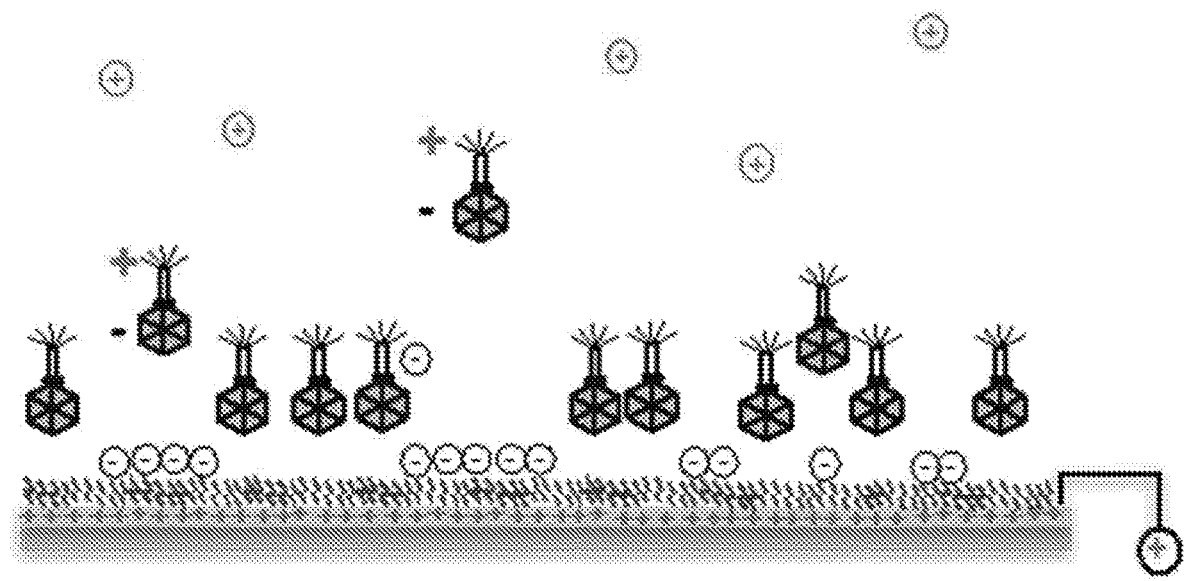
FIGS. 2A-2B and 2D illustrate schematic drawings of the electric-field induced, charge directed immobilization of bacteriophage onto PEI-CNT surface, and the use for bacterial cell detection in FIGS. 2B and 2D.

In embodiments, the system also includes a magnet. As illustrated in FIG. 2A, the magnet is configured to/capable of providing a magnetic field to the sample to separate magnetic particle-coupled bacterial cells from other components in the sample to provide an enriched sample comprising a greater concentration of the target bacteria than the original sample. The phage-functionalized magnetic particles can be used, as described in greater detail below to separate the bacteria of interest from the sample to provide an enriched sample. The "enriched sample" includes a greater concentration of the target bacteria than the original sample.

Figure 2B:
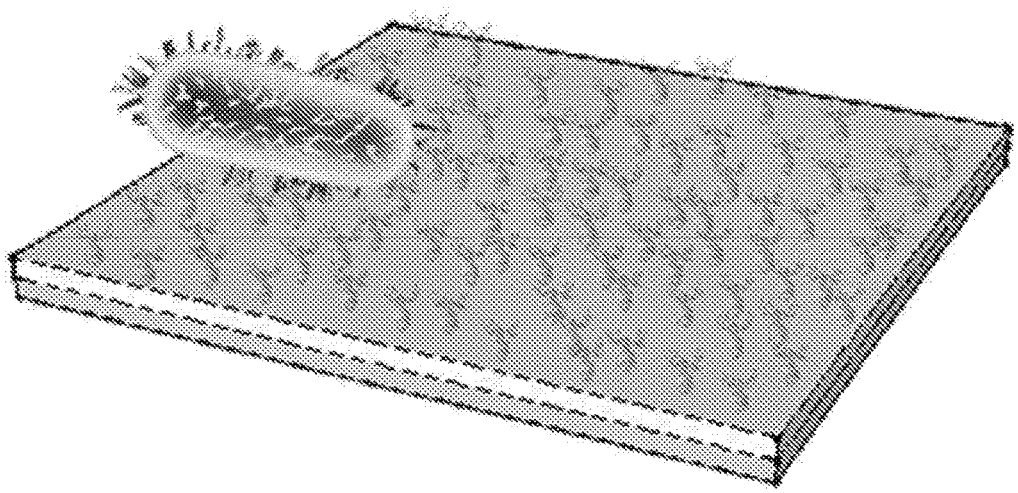
Figures 2C, 2D:
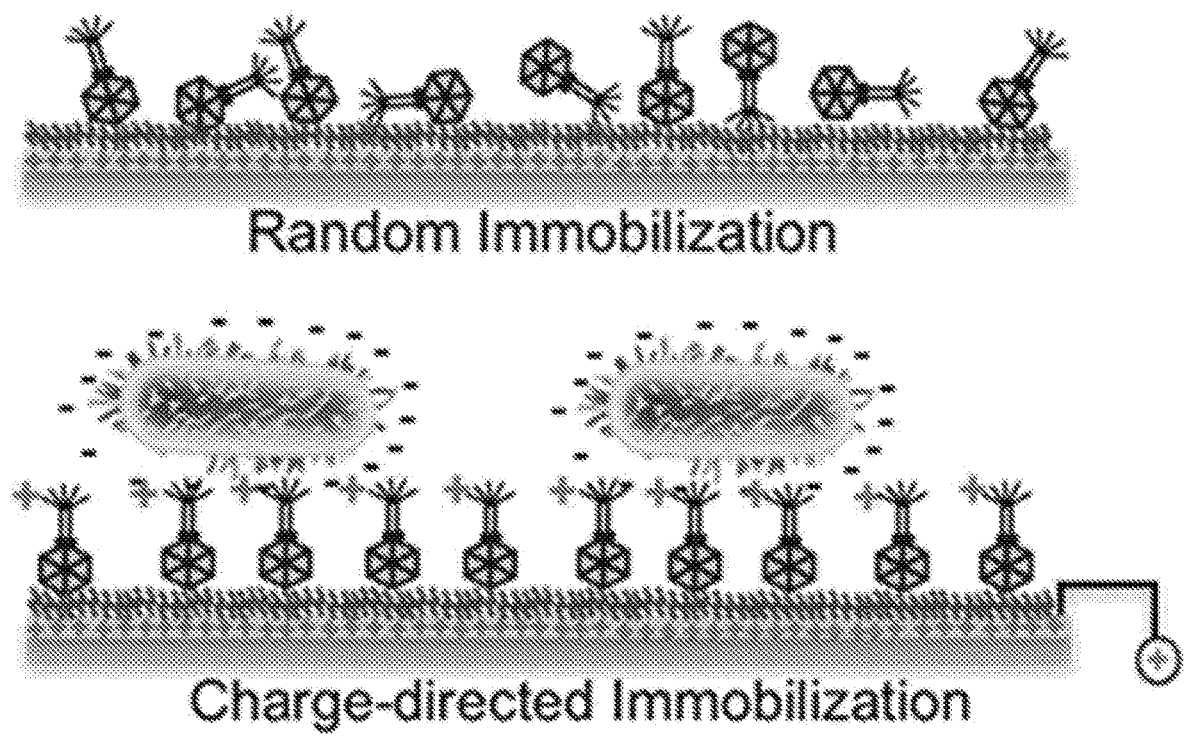
FIG. 2C illustrates random immobilization of bacteriophage onto CNT surface without electric-field-induced immobilization.

Embodiments of the devices and systems of the present disclosure also include a bacteriophage-modified electrode capable of binding the target bacterial cells such as illustrated in FIGS. 2A-2D. In embodiments, the bacteriophage-modified electrode of the present disclosure includes an electrode material or substrate, a transducer material, and a plurality of bacteriophage specific for the target strain of bacteria, where the majority of the phage on the electrode surface are oriented in a head-in, tail-out configuration relative to the electrode surface, as illustrated in FIGS. 2A and 2D, such that a head of the bacteriophage is coupled to the electrode/transducer material, leaving the tail portions free to bind the target bacterial cells as shown in FIGS. 2B and 2D.

In embodiments, the electrode material can include a substrate coupled to a transducer material, such as, but not limited to, an electrically conductive nanostructured material, such as multi-walled carbon nanotubes (MWCNTs). Examples of electrode materials include carbon, gold, platinum, silver, ruthenium, palladium, rhodium, osmium, iridium, or the like. In some embodiments, the nanomaterial transducer material can serve as the electrode and the transducer material. In such embodiments where the nanomaterial serves as the electrode, the substrate does not have to be electrically conductive and can be made of materials including, without limitation, ceramic materials, such as oxides (e.g., silica, fused silica, amorphous silica, fused amorphous silica, sapphire, or the like), nitrides (e.g., silicon nitride, boron nitride, or the like), carbides, oxycarbides, oxynitrides, or the like; polymeric materials (e.g., epoxies, phenolic papers, polyesters, or the like); fiberglass; or the like. In embodiments, the electrode substrate can be carbon, such as, but not limited to a modified screen printed carbon electrode (SPCE).

In embodiments, the nanomaterial transducer material is selected from carbon nanoparticles (e.g., multiwalled carbon nanotubes (MWCNTs)), metal nanoparticles, and metal oxide based nanomaterials. In embodiments, metal nanoparticles can include, but are not limited to, gold, silver, and/or platinum nanoparticles. In embodiments the electrode includes a layer of MWCNTs on a surface of the electrode material. In such embodiments, the plurality of bacteriophages are immobilized to the layer of MWCNT's. In embodiments, the plurality of bacteriophages is attached to the layer of MWCNT on the electrode via a linker coupled to the transducer material (e.g., MWCNTs). The linker can be, but is not limited to, pyrenebutanoic succinimidyl ester (PBSE).

In yet other embodiments, the electrode is modified to have a net positive surface charge, such that free bacteriophage will orient in a head-in configuration to couple to the transducer material. In embodiments, this is achieved, or at least partially achieved, by including a charge-modifying compound coupled to the transducer material on the electrode, wherein the charge-modifying compound has a positive charge, thereby conferring a positive surface charge to the electrode surface. In embodiments, the charge-modifying compound is combined with a transducer material, such as MWCNT's before application of the transducer material to the electrode surface. In other embodiments, the charge-modifying compound is coupled to the transducer material after the transducer material is added to the electrode surface. In embodiments, the charge-modifying compound comprises polyethylenimine (PEI). In embodiments, PEI is combined with MWCNT's such that the PEI is coupled to the CNT's, and then the PEI-modified CNT composition is coated on a surface of the electrode. In embodiments the PEI-MWCNT modified electrode is then also functionalized with a linker compound, such as PBSE for binding to the phage particles. Since PEI has a positive charge, it provides a net positive charge to the electrode surface to encourage the phage particles to bind to the MWCNT surface in a head-in orientation, since the head portion of a bacteriophage carries a negative charge.

In other embodiments, the head-in orientation of the phage is also assisted by use of electric field-induced immobilization to provide a positive charge to the electrode surface. In such embodiments, a positive potential is applied to the electrode to provide a positive surface charge to facilitate charge-directed immobilization of phage to the electrode surface in a head-in, tail-out configuration. In embodiments, electric field-induced immobilization methods are combined with the use of a charge-modifying compound to provide additional charge-directed manipulation of phage particles during the immobilization process. As illustrated in FIG. 2C, without the use of some form of charge-directed manipulation of the phage (e.g., charge-modifying compound or electric field-induced immobilization), the phages couples to the electrode surface in a random orientation. Even with the use of charge-modifying compound alone, some random orientation of phage may occur. The combination of both provides improved probability that a majority of the phage particles will orient in the desired configuration, with head in and tail out.

In embodiments, the system includes both the phage-modified magnetic particles and magnet device to enrich the sample of interest as well as the phage-modified electrode of the present disclosure, such that the enriched sample can be applied to the phage-modified electrode, for detection. In embodiments a first plurality of phage on the magnetic particles binds target bacterial cells in the sample to provide an enriched sample, and then a second plurality of phage on the modified electrode bind the bacterial cells in the enriched sample. Detection of the target bacterial cells then occurs when the electrode produces a detectable electric signal indicating a binding event.

In embodiments of systems of the present disclosure, the system also includes a three-electrode cell, of which the phage-modified electrode of the present disclosure described above is the working electrode. The three-electrode cell also includes counter electrode and a reference electrode in electrochemical communication with the working electrode, and a current-source/potentiostat to provide a current to the cell, such that binding of the target bacteria to the phage-modified electrode produces a detectable impedimetric signal. In embodiments, the potentiostat supplies an electric current to the electrochemical cell and monitor changes in the electric current generated at the working electrode, where binding of target bacteria to the phage-modified electrode produces a detectable impedimetric signal. In embodiments changes in the electric current in the electrochemical cell are recorded as a cyclic voltammogram, differential pulse voltammogram, or other current response to an applied potential or voltage.

In embodiments, the system also includes a signal processing mechanism in operative communication with one or more elements of the electrochemical cell, the signal processing mechanism having data transfer and evaluation software protocols configured to transform raw data from the electrochemical cell into diagnostic information regarding the presence or absence of the target bacteria. In embodiments of bacterial detection systems of the present disclosure, the phage-modified detection electrode of the electrochemical cell is in fluid communication with the phage-modified magnetic bacterial enrichment system described above, such that the enriched sample, produced by phage-assisted specific binding and magnetic separation of target bacterial cells, can be transferred to a detection surface of the phage modified detection electrode.

In embodiments, the signal processing mechanism can be, but is not limited to, a personal computer, a mainframe, a portable computer, a personal data assistant, a smart phone, and a tablet computer, or a combination thereof. In embodiments, the phage-based bacterial detection system of the present disclosure is portable and adapted for sampling in a field environment. Other embodiments include a smart phone application configured to receive information from the signal processing mechanism and transform the information into alerts, recommendations, or both for a user.

In general, detection systems of the present disclosure include additional instrumentation for the system (e.g., signal processing circuitry, a reference electrode, a counter electrode, a potentiostat, and/or an electrochemical workstation), and a signal processing mechanism (e.g., a personal computer, mainframe, portable computer, personal data assistant, or the like), each of which could be in operative communication with one or more of the other components. For instance, in embodiments, the electrochemical sensor systems and phage-based, bacterial detection systems of the present disclosure may include or may be integrated with at least one of the following: a reference electrode and a counter/auxiliary electrode; one reference electrode and one counter/auxiliary electrode for each phage-modified detection electrode in a system; an electrochemical workstation: a signal processing mechanism, wherein the signal processing mechanism comprises data transfer and evaluation software protocols configured to transform raw data into diagnostic information; a temperature control mechanism; or a fluid control mechanism.

By way of example, the phage-based bacterial detection system can be configured such that the phage-modified detection electrode (working electrode) is coupled to counter and reference electrodes and an electrochemical workstation that provides a current or voltage source to the electrodes to affect a flow of electrons to the electrochemical cell that is monitored and measured at the workstation by a computer, which reports and records the voltammetric current. The voltammetric current, and changes therein, can be recorded as a cyclic voltammogram. The computer system can include data transfer and evaluation protocol capable of transforming raw data from the phage-modified detection electrode into information regarding the presence and/or absence of a target analyte (e.g., the target bacteria). The computer can also be capable of providing diagnostic information regarding the target analyte. In certain situations, the computer is a portable personal computer that includes data transfer and evaluation software capable of storing and analyzing the recorded signals. Under these circumstances, the biosensor instrument can provide a diagnostic tool that itself is portable and is powered from the laptop computer. Additional details regarding the methods of using the electrodes, sensors, and enrichment and detection systems of the present disclosure will be described in greater detail below.

Methods of Detecting Bacteria in a Sample

The present disclosure also provides methods of detecting target bacteria (such as, but not limited to, pathogenic bacteria) in a sample of interest (such as, but not limited to, a consumable product). In embodiments the sample is a food or beverage and the target bacteria is a pathogenic bacteria capable of causing disease in humans. In embodiments, the methods of the present disclosure are capable of providing a detectable signal within 1 hour of providing a sample to the phage-modified bacterial detection systems of the present disclosure.

In embodiments, the methods of the present disclosure include sample enrichment and/or bacterial detection methods. In embodiments, the sample enrichment methods include providing magnetic particles functionalized with a first plurality of bacteriophage specific for a target strain of bacteria to be detected. As described above, the bacteriophage specifically binds to a target strain of bacteria. Examples of bacteriophage/bacteria binding pairs include but are not limited to, those provided in the table above. The magnetic particles can be micro- or nanoparticles as described above. The bacteriophages are immobilized to the magnetic particle such that a majority of the phages are oriented in a head-in configuration relative to the magnetic particle such that a head of the bacteriophage is coupled to the magnetic particle. This is accomplished by the methodologies described above, such as, but not limited to using magnetic particles functionalized with linking molecules, genetically modified phage including affinity tags on phage capsid, and the like.

The sample enrichment methods of the present disclosure further include contacting the phage functionalized magnetic particles with a sample of interest. The sample may be from a food or beverage suspected of contamination with a bacterial pathogen, or it may be routine screening of any sample, whether contamination is suspected or not. If the sample is contaminated with the target bacteria (e.g., harbors a detectable amount of such bacteria), the bacteriophage on the magnetic particle surface binds to bacterial cells of the target strain in the sample thereby capturing the target bacteria cells to the phage-functionalized magnetic particles. To produce an enriched sample (for improved detection of bacterial contaminants), the method includes applying a magnetic field to the sample to separate magnetic particle-coupled bacterial cells from other components in the sample. After such separation, the bulk of the sample (containing other components) can be discarded, leaving an enriched sample having a greater concentration of the target bacteria than the original sample.

Methods of the present disclosure also include phage-based detection methods. These methods can be used in conjunction with the enrichment methods described above or with other samples. Detection will be quicker and more efficient when used with an enriched sample, produced by the methods of the present disclosure or otherwise enriched with other methods.

In embodiments, detection methods of the present disclosure include contacting a sample (e.g., an enriched sample) with a bacteriophage-modified electrode of the present disclosure described above. As described in greater detail above, the bacteriophage-modified electrode of the present disclosure includes an electrode material modified with a transducer material (e.g., a nanostructured transducer material such as MWCNTs), where the transducer material is on a surface of the electrode material. The electrode further includes a plurality of bacteriophage specific for the target strain of bacteria. As described above, the majority of the phage on the electrode are oriented in a head-in, tail-out configuration relative to the electrode surface such that a head of the bacteriophage is coupled to the transducer material (e.g, MWCNTs). This can be accomplished by the methods and materials described above. The plurality of bacteriophage immobilized to the electrode surface/transducer material are capable of binding the target bacteria in the enriched sample. The detection method further includes applying a current to the bacteriophage-modified electrode such that binding of the target bacteria to the phage-modified electrode produces a detectable impedimetric signal. If used in conjunction with the enrichment methods of the present disclosure, the plurality of bacteriophage on the magnetic particles can be referred to as a first plurality of bacteriophage and the plurality of bacteriophage on the electrode can be referred to as a second plurality of bacteriophage. In embodiments, the first and second plurality of bacteriophage may be the same strain/type of bacteriophage, e.g., a bacteriophage specific for the target bacteria. However, the first plurality of bacteriophage may be further genetically modified to include an affinity tag for coupling the phage to the magnetic particle surface. The detection methods of the present disclosure also include applying a current to the electrode and monitoring changes to identify binding between the bacteriophage and target bacterial cells. Thus, the detection system also includes elements of an electrochemical cell/sensor along with signal processing mechanisms and software for its use.

When the enrichment and detection methods are used together, the method also includes transferring the enriched sample to the phage-modified electrode/detection device/system. In embodiments, both methods may be performed in a single, integrated system. The system may also include signal processing mechanisms to provide output, and such systems may be mobile to provide mobile detection methods for a field testing (e.g., on site) environment.

As described above, the phage-modified electrochemical sensors of the present disclosure are capable of providing a specific electrochemical excitation signal that is optimized to yield the maximum diagnostic value. These systems thus can represent a complete detection package with the capability to aid rapid analysis by a person who has minimum technical training. In exemplary embodiments, the raw electrochemical output from the electrochemical sensor of the present disclosure is collected and transferred to the memory of a computer, which includes a pattern recognition evaluation program that can be "trained" to identify a specific binding event and also the degree of the matching between the capture molecule and the target analyte (e.g., target bacterial pathogen), and thus recognize the signature of a particular binding event for which it was "trained". Such a detection system provides a complete package whose purpose is to aid rapid screening, detection, and analysis of a target analyte, without elaborate preparation, by a person who has minimum technical training and to enable portability of such a system, bringing heretofore unavailable diagnostic and monitoring capabilities to large and/or remote areas.

The various electrodes can be in operative communication with an electrochemical workstation that provides a current or voltage source to the three electrode cell. This provides a flow of electrons to the three-electrode cell(s) that is monitored and measured at the workstation by a signal processing mechanism, which reports and records the voltammetric current. The voltammetric current, and changes therein, can be recorded as a cyclic voltammogram. The workstation may provide a voltage source to the electrode and measure a current, but it is also capable of working in reverse providing a current source and measuring a voltage. Either set-up is acceptable for operating the biosensor instruments of the present disclosure.

The signal processing mechanism can be a personal computer, mainframe, portable computer, personal data assistant, or the like. The signal processing mechanism can include data transfer and evaluation protocol capable of transforming raw data from the biosensor array into information regarding the presence, absence, and the extent of the interaction of a target bacterial cell(s). The signal processing mechanism can also be capable of providing diagnostic information regarding the target bacterial cell(s).

Generally, the solid state electronics, including, for example, a potentiostat circuit connected to working and reference electrodes, as described above for performing electrochemical measurements, are external to the phage-modified detection electrode (and any printed circuit board package associated with the phage-modified detection electrode to enable connection to other elements of an electrochemical cell potentiostat circuitry, etc.). Notwithstanding this, the phage-modified detection electrode, reference, and counter/auxiliary electrodes, electrochemical workstation, and signal processing mechanism can be arranged in a variety of configurations, when in combination with other components that are known to those of skill in the art.

Again, the phage-modified detection electrode can also include signal processing circuitry, as discussed above. The electrode is then contacted with a sample to be analyzed (e.g., in sufficient contact with the sample for a target bacterial cell contained in the sample to interact with the bacteriophage on the phage-modified detection electrode), and the system is interrogated using standard electrochemical techniques. As discussed above, the electrochemical sensor/detection system includes a current source to provide a flow of electrons to drive the electrochemical processes at the phage-modified detection electrode and a signal processing mechanism for detecting and reporting any change at the electrode. As discussed above, some embodiments of the phage-modified detection system also include a data analysis component (e.g., data analysis software on a computer system coupled to the biosensor array described above) for storing and evaluating the electrochemical signal produced by the phage-modified detection electrode.

Additional details regarding the methods and compositions of the present disclosure are provided in the Examples below. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Now having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure Example 1—Charge Directed Immobilization of Bacteriophage on Nanostructured Electrode for Bacterial Cell Electrochemical Biosensors The present example describes development of a new type of carbon nanotube (CNT)-based impedimetric biosensor for rapid and selective detection of live bacteria. Studies were conducted using T2 bacteriophage-based biosensor for the detection of *Escherichia coli* B. The T2 bacteriophage (virus) served as the bio-recognition element which was immobilized on polyethylenimine (PEI) functionalized carbon nanotube transducer on glassy carbon electrode. Charge-directed, orientated immobilization of bacteriophage particles on carbon nanotubes was achieved through covalent linkage of phage-capsid on to the carbon nanotubes. The presence of the immobilized phage on carbon nanotube modified electrode was confirmed by fluorescence microscopy. Electrochemical impedance spectroscopy (EIS) was used to monitor the changes in the interfacial impedance due to the binding of *E. coli* B to T2 phage. The detection was highly selective towards the B strain of *E. coli* as no signal was observed for the non-host K strain of *E. coli*. The detection limit of the biosensor is $10^3$ CFU/mL Experimental Section
Materials and Instruments The following chemicals were purchased and used without further purification: sodium chloride and sodium phosphate dibasic (both from EMD chemicals), potassium dihydrogen phosphate (BDH), magnesium sulfate heptahydrate (J.T. Baker), 1-pyrenebutanoic acid, succinimidyl ester (PBSE) (Sigma Aldrich), polyethylenimine (PEI) (Sigma Aldrich), yeast extract and agar powder (all from Alfa Aesar), tryptone (Amresco). Multi-walled carbon nanotubes (CNT) (diameter 8-15 nm) was obtained from Cheap Tubes Inc. SM buffer was prepared by mixing 5.8 g of NaCl, 2 g of $MgSO_4.7H_2O$, 50 mL of 1M Tris-HCl pH 7.5, and 1 mL of 10% (w/v) gelatin in deionized water. Luria-Bertani (LB) medium was prepared by mixing 10 g of tryptone, 5 g of yeast extract and 10 g of NaCl in deionized water and adjusted to pH 7.0. LB-agar medium was prepared by adding 6 g of agar to 400 mL of LB media. 2 g of agar was added to 400 mL of LB media to obtain soft agar medium. 10× phosphate buffered saline (PBS) was prepared by mixing 16 g NaCl, 0.40 g KCl, 2.8 g $Na_2HPO_4$, and 0.49 g $KH_2PO_4$ in 200 mL deionized water yielding a buffer solution of pH 7.4. The prepared PBS was further diluted to 1× before use. All media, buffer and glassware were sterilized before use. *E. coli* B and T2 phage were purchased from ATCC (11303 and 11303-B2, respectively). *E. coli* K strain was kindly provided by Dr. Yajun Yan (University of Georgia, Athens). Glassy carbon electrode (GCE) obtained from CH Instruments was used for all electrochemical experiments (3 mm diameter).

Scanning electron microscopy (SEM) images of the modified electrode were obtained using FEI Inspect FEG electron microscope. Attenuated Total Reflectance-Fourier transform infrared spectroscopy (ATR-FTIR) measurements were performed on carbon nanotube coated silica wafer in Nicolet 6700 instrument. Fluorescence images were obtained using EVOS fluorescence microscopy (Invitrogen). Surface charge of carbon nanotubes, bacteria and phage particles were analyzed by ZetaSizer (Malvern). Contact angle measurements to determine hydrophobicity of the CNT electrodes before and after PEI functionalization were performed by a KrüSs DSA 100 using a 1 μL drop of 18 MΩ water (pH 7).

Bacteria Preparation and Phage Propagation

*E. coli* B (ATCC 11303) were grown in 4 mL of LB medium overnight at 37° C. 1 mL aliquot of the overnight culture was inoculated into 100 mL of fresh LB, followed by incubation for 3 h at 37° C. in an incubator shaker. 1 mL of the culture was then centrifuged at 4000 g for 10 min to remove medium and washed with 1×PBS buffer for twice before each experiment. Enumeration of bacteria was performed by plate count techniques and expressed in CFU/mL.

T2 bacteriophage (wild type) was amplified using soft agar overlay techniques. T2 bacteriophage (wild type) was amplified using soft agar overlay techniques. Briefly, 250 μL of bacterial host and 100 μL of phage stock (~$10^{10}$ PFU/mL) were added to molten soft agar (LB containing 0.5% agar), poured onto LB plates (previously prepared and incubated under 37° C.) and incubated overnight at room temperature. SM buffer was then added to the plates and the plate was shaken for two hours. The soft agar layer was scraped off the surface and was centrifuged at 4000 g for 10 min to remove agar and bacteria debris. The supernatant was passed through a 0.22 μm Millipore filter to remove any remaining bacterial cells, followed by centrifugation at high speed 17200 g at 4° C. for three hours. The supernatant was removed and the phage pellet was re-suspended in SM buffer. Plaque assay was applied to measure the phage titer and was expressed in PFU/mL prior to use. Briefly, phage was serially diluted with 1×PBS buffer and added to a test tube containing 3 mL molten soft agar (0.5%) with 250 μL of *E. coli* B host culture. The solution was poured over LB agar plate and incubated overnight at room temperature. The visible plaques were counted the following day.

Preparation of PEI-Functionalized CNT

Multiwall carbon nanotubes (CNT) were functionalized with polyethylenimine (PEI) to obtain positive surface charge as previously reported (see, Li et al., 2013, which is hereby incorporated by reference herein). The PEI functionalized carbon nanotube (PEI-CNT) modified GCE was used as the working electrode. Briefly, carboxyl functionalized multi walled CNT (COOH-CNT) was synthesized by adding 40 mg CNT to concentrated 20 mL HNO$_3$ and H$_2$SO$_4$ (1:3, v/v) solution at 120° C. in an oil bath to react while string for 30 min. The product was then washed with DI water to a neutral pH and vacuum dried at 70° C. For preparation of PEI-CNT, 30 mg COOH-CNT was dissolved in 15 mL dry DMF following which the suspension was sonicated for 5 min and 6 mL SOCl$_2$ was added gradually in an ice-bath to acylate the COOH group. After 24 h reflux at 120° C. with continuous stirring, the reaction mixture was centrifuged at 10000 rpm. The pellet was washed with anhydrous THF, dried under vacuum at room temperature for 2 h. The pellet was then resuspended into 5 mL of DMF. After string for 1 h under N$_2$ atmosphere at 90° C., 100 mg PEI was added into reaction flask and reacted with acylated COOH-CNT for 3 days. Finally, the reaction mixture was centrifuged, washed with methanol and dried at 70° C.

Phage Immobilization and Electrode Preparation

To facilitate phage immobilization onto CNT modified electrode surface, a positive potential was applied on working electrode for phage deposition, followed by covalent linkage of phage through PBSE onto PEI-CNT (FIG. 2A). The tethering agent PBSE adheres non-covalently to CNT and covalently to the proteins in the phage capsid, thereby linking the phage and CNT for irreversible attachment (Ramasamy, et. al., 2010). 2 mg of PEI functionalized multiwall carbon nanotube (PEI-CNT) was dispersed in 1 mL deionized water. The suspension was ultra-sonicated for 10 min prior to use. 12 μL PEI-CNT was dropcast on glassy carbon electrode (GCE) surface and dried. Prior to phage attachment, the PEI-CNT modified GCE was activated with succinimidyl ester (PBSE) as molecular tethering agent.[28-32] 4 μL of 10 mM PBSE solution (in DMF) was dropcast on electrode and allowed to react for 15 min on ice. The excess unreacted PBSE was removed by rinsing the electrode with DMF, followed by PBS buffer. For electric field-induced immobilization, a positive potential of +0.5 V vs Ag/AgCl was applied to the working electrode in a 1×PBS buffer solution containing with bacteriophage (~10$^9$ PFU/mL) for 1 h to facilitate the charge-directed immobilization process. Finally, the electrode was rinsed using SM buffer and covered with 50 μL E. coli B suspension for 30 min. After rinsing with buffer, the phage modified CNT electrode was used as a biosensor to perform electrochemical impedance measurements. For control experiments, the biosensor was tested in the presence of only buffer, only bacteria and buffer containing E. coli K strain, which is not a host bacteria for T2 phage. Seven-fold serial dilutions (10$^2$-10$^8$ CFU/mL) of E. coli B were prepared for bacterial cell detection experiments.

Fluorescence Imaging of Bacteria and Phage

To characterize the surface immobilized phage, 100 μL phage (10$^{10}$ PFU/mL) was stained with SYBR gold, a fluorescent nucleic acid dye with EX/EM of 495 nm/537 nm, at a final concentration of 5× for 20 min at room temperature. Prior to the electric field-induced attachment of phage onto electrode surface, any free dye on phage particles was removed by diluting 100 μL of the phage suspension and then centrifuging the sample across a 100 kDa (EDM Millipore, UFC 910008) filter four times. Each centrifugation step led to a 40-fold of dilution of dye, reducing the final concentration of dye. After 4-step of centrifugation, the phage was resuspended in saline to the original volume of 100 μL.[33] Phage was then added to electrochemical cell for electric field-induced immobilization experiments using CNT coated ITO glass slide as working electrode, since rod-shape glassy carbon electrode is not suitable for fluorescence imaging. Same experimental procedures were applied to immobilize phage onto ITO surface in dark. The resulting ITO was used for fluorescence characterization (See detailed method in the Supporting Information) (Van Valen, et al., 2012).

Infectivity of Immobilized Phage

Phage immobilized CNT coated ITO glass slide was prepared using the same method to study the infectivity of the immobilized phage. The infectivity of the immobilized phage was verified using the disk diffusion technique as reported in Andrews, et al., 2009 (herein incorporated by reference herein). The plates were inspected the subsequent day for lysis rings around the disks. ITO glass slides with no phage were used as a negative control.

Electrochemical Characterization

Electrochemical characterization was conducted using CHI-920c model potentiostat (CH Instruments inc, Austin, Tex.). A conventional three-electrode cell (a working electrode, an Ag/AgCl reference electrode and a Pt wire auxiliary electrode) was used for electrochemical measurements. All the electrochemical measurements were carried out at 25° C.±2° C. in a 5 mL voltammetry cell containing 5 mM Fe(CN)$_6^{3-/4-}$ (1:1) mixture in 1×PBS buffer, unless otherwise stated. Impedance was measured at the open circuit potential, with a superimposed AC voltage of amplitude 5 mV between frequencies 100 kHz and 10 Hz.

Characterization of Surfaces, Bacteria and Phage

Scanning electron microscopy (SEM) images of the modified electrode were obtained using FEI Inspect FEG electron microscope. Attenuated Total Reflectance-Fourier transform infrared spectroscopy (ATR-FTIR) measurements were performed on carbon nanotube coated silica wafer in Nicolet 6700 instrument. Fluorescence images were obtained using EVOS fluorescence microscopy (Invitrogen). Surface charge of carbon nanotubes, bacteria and phage particles were analyzed by ZetaSizer (Malvern). Contact angle measurements to determine hydrophobicity of the CNT electrodes before and after PEI functionalization were performed by a KrüSs DSA 100 using a 1 μL drop of 18 MΩ water (pH 7)

Results and Discussion

PEI-Functionalized CNT Characterization

Figure 3:
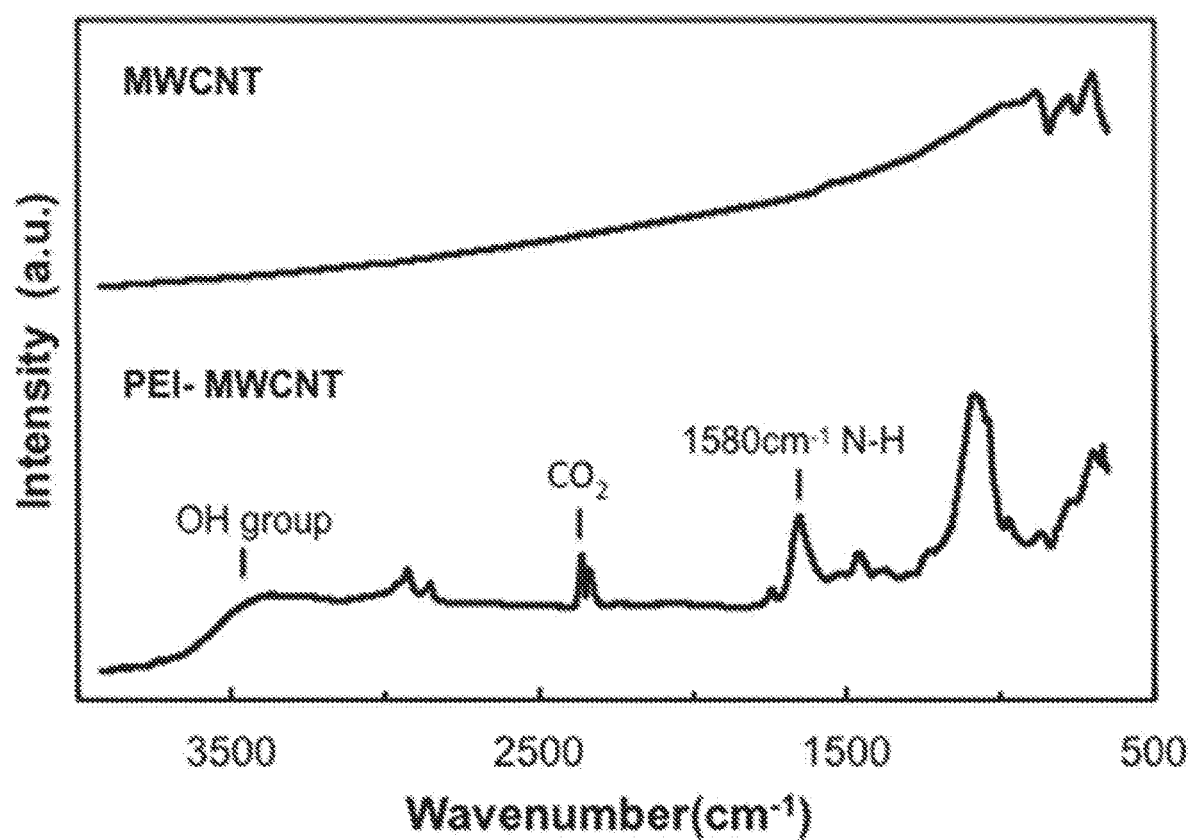
FIG. 3 is an ATR-FTIR spectrum confirming the successful modification of MWCNT with PEI.

To confirm the successful functionalization of PEI on CNT, ATR-FTIR measurements of the modified electrode were performed to study the peaks characteristic of the functional groups on the CNT surface and the resulting spectra are shown in FIG. 3. The presence of carboxylic groups on CNT (from the acid treatment) was confirmed by C=O stretching vibration at 1690 cm$^{-1}$ as well as O—H stretching vibration at 3440 cm$^1$. In addition, two absorption peaks at 2988 and 2893 cm$^{-1}$ in the spectra could be assigned to CH$_2$ stretching in the alkyl chain of PEI. The peak at 1580 cm$^{-1}$ represent the N—H deformation vibration of primary amine group present in PEI-CNT. Peaks corresponding to CN stretching was also observed between 1107 and 1134 cm$^{-1}$. The identification of these peaks confirms the successful functionalization of CNT with PEI.

Figure 4:
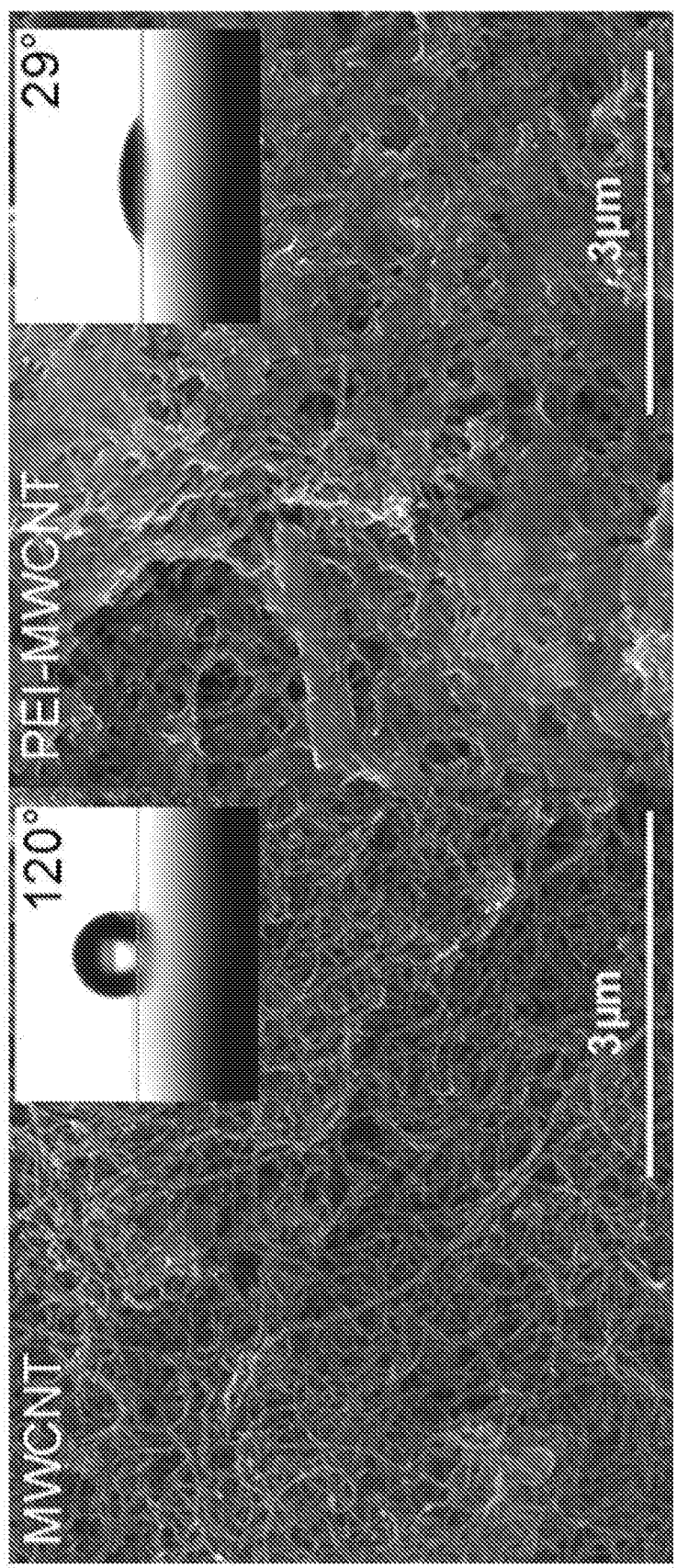
FIG. 4 illustrates SEM images of CNT before (left) and after (right) PEI modification. Inset: Images of water droplet on the substrates and their contact angles.

FIG. 4 shows the SEM images of CNT before (left) and after (right) PEI modification. Some aggregation occurred after PEI functionalization of CNT, with formation of many mesopores as shown in the right-hand image in FIG. 4. The surface amine functional groups increased the surface energy and make the surface more hydrophilic resulting in the low contact angle of 29° (see inset in FIG. 4) for contact between water droplet and the surface. On the other hand, the surface functional groups also altered the surface charge and the zeta potential of CNT. The zeta potentials of CNT, PEI-CNT in pH 7.4 PBS were −20.2±0.7 mV and +12.4±0.8 mV, respectively, as shown in Table 1.1, below. Positively charged PEI-CNT hence prepared was used as for the immobilization of negatively phage particles in further studies.

TABLE 1.1

Zeta potentials of biological particles and carbon nanotubes measured in pH 7.4 PBS saline.

| Sample | Zeta Potential (mV) |
|---|---|
| E. coli (ATCC 11303) | −9.7 ± 1.1 |
| Phage (ATCC 11300-B2) | −10.0 ± 0.8 |
| Unmodified CNT | −20.2 ± 0.7 |
| PEI-CNT | +12.4 ± 0.8 |

Characterization of Immobilized Bacteriophage

Zeta potential measurements elucidate the surface charge and colloidal stability of biological particles. The zeta potential of T2 phage in PBS buffer was measured as −10.0±0.8 mV, resulting in a net negative charge (Anany, et al., 2011). E. coli (ATCC 11303) has zeta potential of −9.7±1.1 mV. In order to achieve the highest capture efficiency of bacteria with immobilized phage particles, T2 phage particles can be immobilized with its positively charged tail-spike proteins exposed to negatively charged bacterial cells. The heads in—tail out fashion on the electrode helps orient the phage towards bacterial cell capture by the exposed tail fibers and this orientation is facilitated through PEI functionalization of CNT and subsequent electric field-induced deposition of phage onto PEI-CNT. FIG. 2A shows the electric field-induced immobilization of phage particles onto the surface of positively charged PEI functionalized CNT, which was also functionalized with a hetero-bifunctional molecular tethering agent PBSE. The aromatic pyrene moiety of the PBSE interacts with CNT side walls through π-π stacking as demonstrated in our previous work (Ramasamy, et al., 2010; Sekar, et al., 2014; Umasankara, et al., 2013; Zhou, et al., 2015), while NHS ester moiety binds with primary amine groups in the protein (of T2) to form amide bonds. The PBSE based method for protein immobilization on CNT has been studied with various enzymes, but little work has been related to phage particles immobilization (Li, et al., 2013). During electric field-induced immobilization, an electrical double layer could form in the proximity of electrode surface on which the phage is deposited (FIG. 2A). The formation of this negative ion layer may decrease the intensity of the electric filed inside the electrolyte, resulting in disorientation of phage particles. The orientation of the phage particle are related with Debye length ($\kappa^{-1}$) on the CNT surfaces (Richter, et al., 2016). The phage particles will align along the lines of the electric field within the volume when $\kappa^{-1}$ is larger than the size of the phage. When $\kappa^{-1}$ is smaller than the size of phages, the orientation of the phage particles occurs due to electrostatic interaction (Sadeghi, et al., 2011; Zweckstetter, et al., 2004. In the present case, T2 phage is much larger than the $\kappa^{-1}$ (few nanometers). Thus, the immobilized phages were preferentially attached on to the CNT modified electrode in head in-tail out orientation as shown in FIGS. 2A and 2D.

To further visualize bacteriophage on electrode surface, T2 bacteriophage were labeled using a DNA intercalating SYBR Gold dye. For a duration of 1 h and phage concentration of $10^9$ PFU/mL, +0.5 V vs Ag/AgCl was applied to the PEI-CNT electrode. Fluorescence images are shown in FIGS. 5A-4D. The images in FIGS. 5A-4B confirm the successful electric field-induced deposition of bacteriophages onto PEI-CNT. Several phage particles were observed and counted. Control experiment was performed as shown in FIGS. 5C-5D using covalent linkage only (no voltage applied), where phages were incubated with PBSE activated CNT surface for 2 h. In this case, only a few phage particles were observed in the fluorescence image. No phage particles were observed in the negative control (in the absence phage) (data not shown). The fluorescence seen in negative controls is due to the autofluorescence of the CNTs which is well established in the literature (Zhou, et al., 2007). The higher intensity of the CNT in negative control images (not shown) can be explained due to the higher intensity used while imaging and also from the fact that it is in the focal plane as opposed to FIGS. 5A-5D, where the CNT are out of focus. From these results, it can be concluded that the electric field-induced deposition significantly increased the population of surface immobilized phage particles, which results in a high bio-receptor loading on the electrode surface for host bacterial cell detection.

Figure 6B:
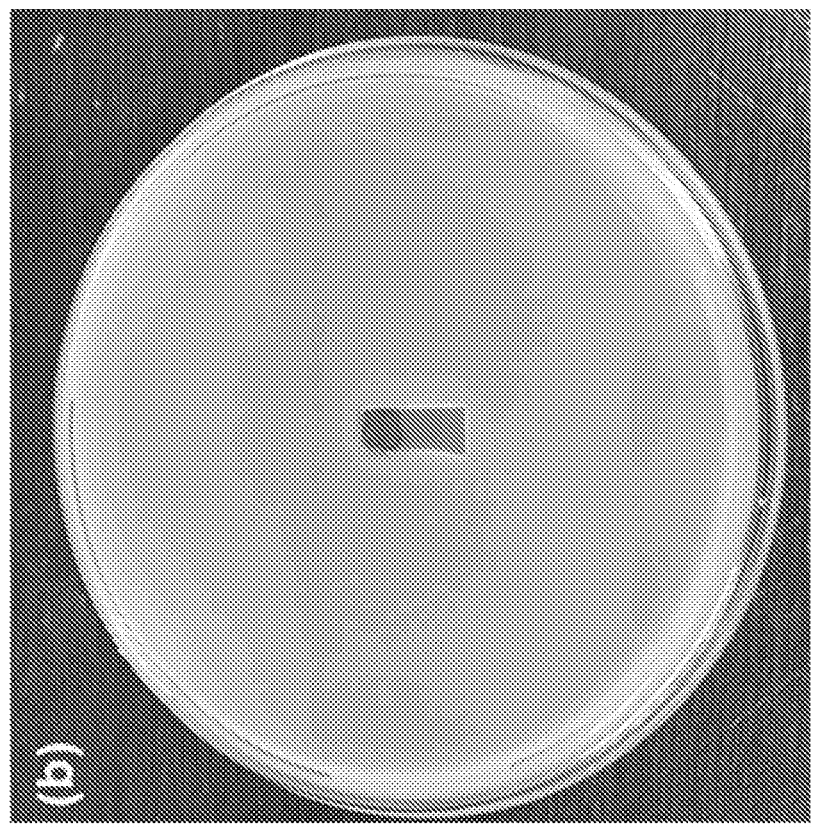
FIGS. 6A-6B are digital images of petri dishes that illustrate the infectivity of immobilized phage.
Figure 6A:
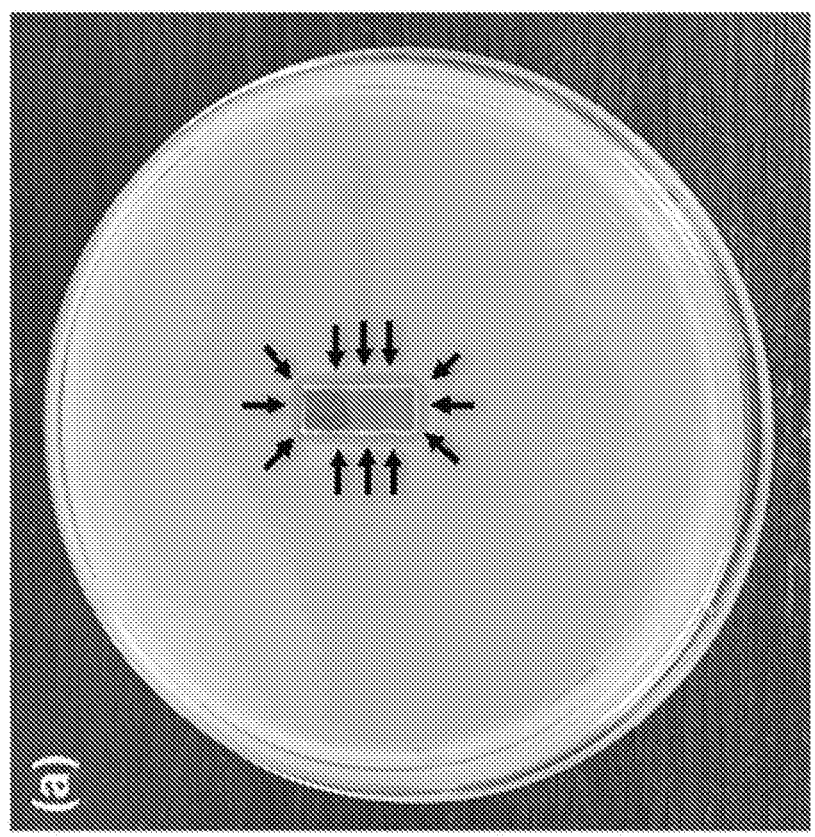

Since there is no feasible and reliable method for estimating the number of the receptors on the electrode surface, the activity of the immobilized phages was verified for their infectivity using disk diffusion method (Andrews, et al., 2009). For this, a flat electrode should be used to conduct the same electric field-induced immobilization of phages. A CNT-coated ITO glass was applied as working electrode which was further incubated on a lawn of bacteria using soft agar overlay method. As shown in FIG. 6A, lysed rings were found around the ITO electrode with immobilized phages, whereas ITO electrode without phage in FIG. 6B showed no lysis ring. The results indicate that the immobilized phages were able to lyse (kill) bacteria cells and were thus deemed active and infective. The T2 phage modified PEI-functionalized CNT nanostructured electrode was then evaluated as a biosensor for the detection of E. coli B using impedance electrochemical impedance spectroscopy.

Electrochemical Characterization and Bacteria Detection

Electrochemical impedance spectroscopy (EIS) was used to further characterize the assembly of the biosensor in a PBS (pH 7.4) containing 5 mM $Fe(CN)_6^{3-/4-}$ as the redox couple. EIS was reported as an effective and non-destructive method to monitor electrode surface characteristics. In the presence of $Fe(CN)_6^{3-/4-}$, the impedance measured is Faradaic impedance of the redox couple. The results of Nyquist plot ($-Z_{im}$ vs $Z_r$) of bare PEI-CNT and phage modified PEI-CNT in the presence of 5 mM $Fe(CN)_6^{3-/4-}$ redox couple in PBS (pH 7.4) are not shown. The results illustrated that electric field-induced deposition of phage achieved higher loading of phage particles on the electrode surface compared to non-EFI immobilization. The high phage loading on CNT could help to enhance the biosensor performance as evaluated and discussed below.

Figure 7A:
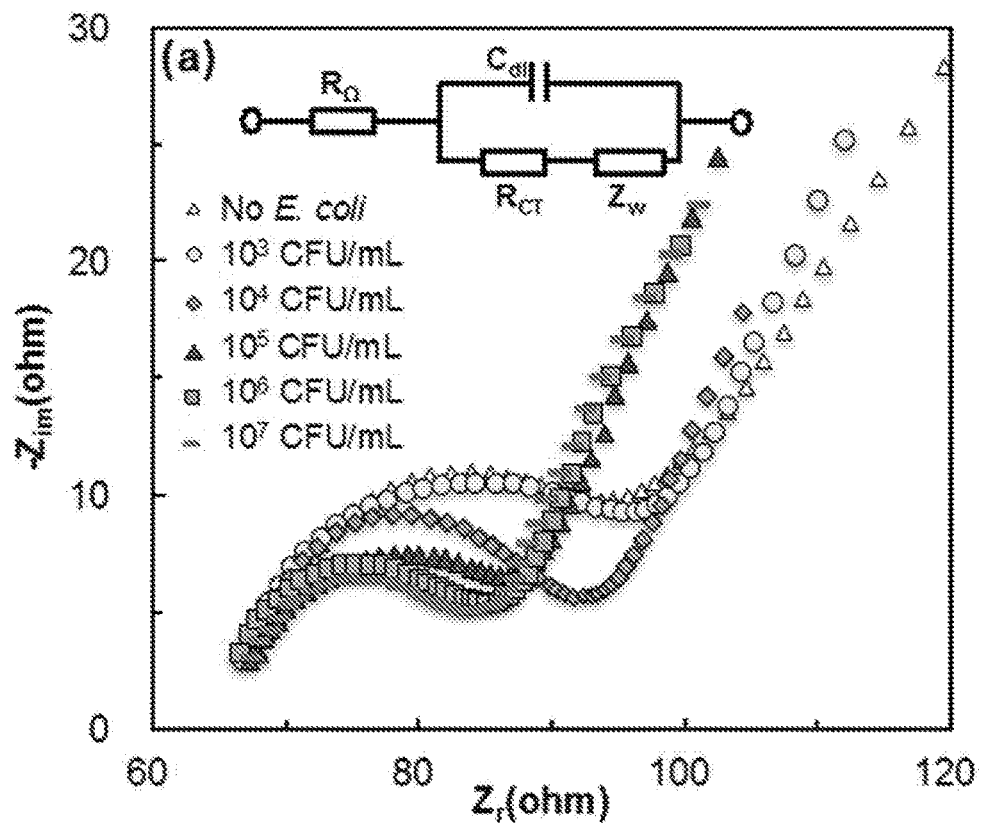
FIG. 7A is a Nyquist plot for T2 page-modified electrode in the absence and presence of *E. coli* B at different concentrations. (Inset: Randles equivalent circuit)

FIG. 7A illustrates the representative Nyquist plots of the impedance spectra of the phage-modified nanostructured electrode of the redox couple obtained both in the absence and presence of bacteria (at different concentration expressed in CFU/mL). The equivalent circuit, also called Randles equivalent circuit, used to fit the Nyquist data is also shown as an inset in FIG. 7A. This model consists four circuit elements, including electrolyte resistance ($R_\Omega$), charge transfer resistance ($R_{CT}$), double layer capacitance ($C_{dl}$), and Warburg impedance ($Z_w$). Among them, $R_\Omega$ and $Z_w$ represent the properties of the electrolyte solution and the mass transfer of the redox probe in the solution, respectively. $C_{dl}$ represent a nonlinear capacitance on the electrochemical interface. The arc of the Nyquist plot reflects the charge transfer resistance $R_{CT}$, which is determined by the type of surface modification, the kinetics of the reaction and the dielectric and insulating properties on the electrode surface. The capture of bacterial cells on phage-modified electrode surface could alter the surface properties of electrode which in turn vary the impedimetric measured on the biosensor electrode.

To evaluate the sensitivity of the biosensor, the phage-modified nanostructured CNT electrode was used for the detection of $E.$ $coli$ B from its suspensions of different concentrations ($10^2$-$10^8$ CFU/mL). The bacterial cell suspensions were incubated on the phage-modified electrode surface then rinsed before the AC impedance measurements. Impedance measurements were made at different $E.$ $coli$ B concentrations and the results were compared with that of the control where no $E.$ $coli$ was present. As shown in FIG. 7A, the diameter of the Nyquist are decreased with increasing bacterial cell concentration suggesting a direct influence of bacterial cell attachment on the impedance of the above redox reaction. A significant variation was observed in $R_{CT}$ upon the $E.$ $coli$ attachment onto phage modified nanostructured electrodes, and the difference is amplified at high $E.$ $coli$ concentrations (see magnitude of the are in FIG. 7A). Other parameters such as $R_\Omega$, $C_{dl}$ and $Z_w$ did not vary significantly as a result of $E.$ $coli$ capture on to the electrode.

In many impedimetric biosensors, charge transfer resistance usually increases with increasing $E.$ $coli$ concentration (Tlili, et al., 2013; Shabani, et al., 2013; Bekir, et al., 2015; Li, et al., 2014)). Such increase in $R_{CT}$ due to $E.$ $coli$ attachment could be attributed to the lowering of redox kinetics at the interface, as $E.$ $coli$ could act as a barrier on the electrode blocking the accessible CNT sites for Fe(CN)$_6^{3-/4-}$ redox reaction. In this case, a considerable decrease of charge transfer resistance was observed after 30 min contact between surface immobilized phage and $E.$ $coli$. To completely understand the relation between charge transfer resistance and surface attached bacterial cells, a live/dead cell viability assay was performed to study the interaction between bacteria cells and surface immobilized phage particles. According to the fluorescence image shown in FIG. 7, the immobilized T2 effectively disturbs the integrity of the cell membrane with increasing incubation time.

Figure 7B:
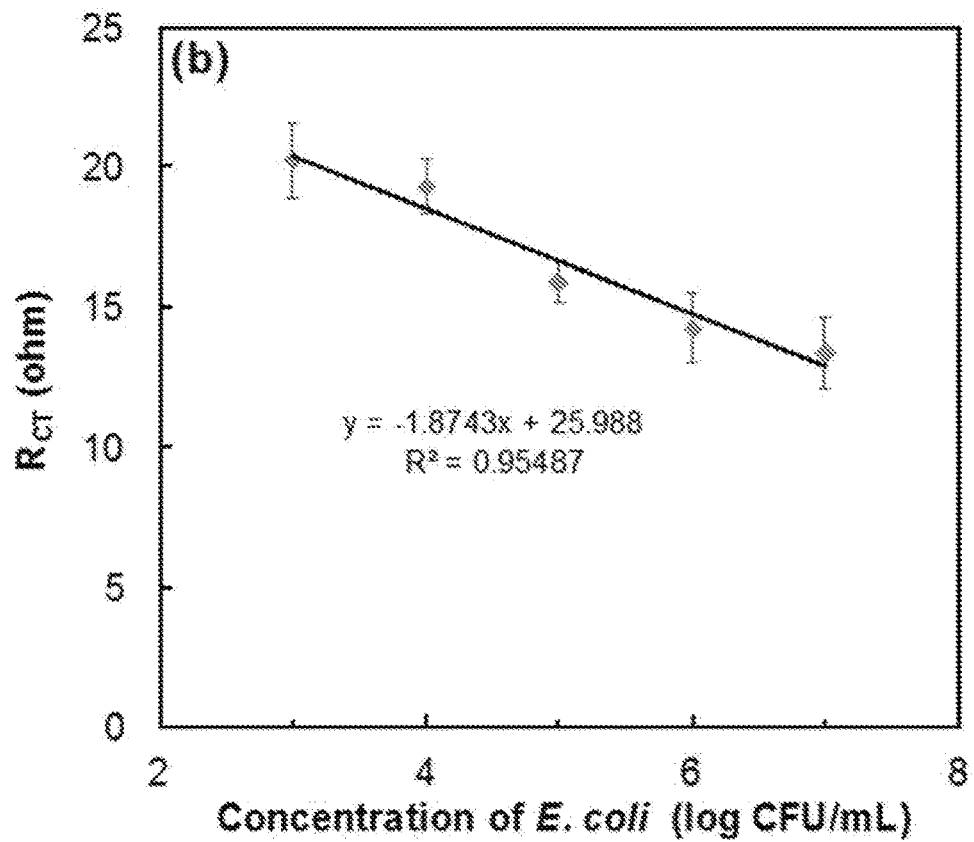
FIG. 7B illustrates variations of charge transfer resistance at different *E. coli* B concentration in the sample.

The images in FIG. 7 show a progressive decrease of green fluorescence (viable $E.$ $coli$ cells) and increase of red fluorescence (dead $E.$ $coli$ cells) due to phage infection. A distinct change in viable $E.$ $coli$ cells were noticed after 20 minutes and the cells were completely compromised after 25 min, suggesting the infection time of $E.$ $coli$ and the lytic cycle of immobilized phages was around half an hour. It is reasonable to assume all $E.$ $coli$ cells that remained on the electrode surface were attached to phage particles. However, not all bacterial cells were compromised at the same time. The released phages from lysed cells may further infect surrounding bacterial cells resulting in increasing number of red fluorescence. Above all, immobilization of phages onto electrode surface shortened the latent period of phage. In electrochemical impedance measurements, the impedance data were collected after 30 min contact between phages and bacterial cell. The lysis of bacteria may take place with the release of intracellular constituents, such as potassium ions and sodium ions during the incubation time. The increasing amount of ions on electrode surface many leads to higher conductivity which results in decrease of $R_{CT}$ with increasing $E.$ $coli$ concentration. This finding was in agreement with the findings by Shabani et al. (2008). Further studies are still needed to better understand the role of the immobilized phage lysing ability. At a cell concentration of $10^7$ CFU/mL, the change in charge transfer resistance is insensitive to changes in cell concentration, which may be due to surface saturation of adhered cells. A linear correlation between $R_{CT}$ and the bacterial concentration was observed between $10^3$ and $10^7$ CFU/mL as shown in FIG. 7B. No significant variation in $R_{CT}$ was observed for concentrations below $10^2$ CFU/mL in a 50 µL $E.$ $coli$ suspension. The detection takes less than 40 min. The detection limit of this biosensor was then found to be $10^3$ CFU/mL in a 50 µL $E.$ $coli$ volume.

The sensitivity of bacterial detection by phage-based biosensor could be influenced by the type of immobilization method used for attaching phage to the electrode surface as reported in the literature (Arya, et al., 2011; Shabani, et al., 2008; Shabani, et al., 2008; Singh, et al., 2009; Pearson, et al., 2013; Ahn, et al., 2014; Tolba, et al., 2010. In the present study, the phage-based biosensor achieved a detection limit of $10^3$ CFU/mL for $E.$ $coli$ B, which is better than most impedimetric sensors previously reported (Tlili, et al., 2013, Shabani, et al., 2013; Bekinr, et al., 2015; Li, et al., 2014). Bacteriophages were treated as charged particles which could be deposited onto working electrode. By electric field-induced immobilization, an increasing number of phage particles could be aligned onto electrode surface. More importantly, the surface cationic polymer modified CNT interacts with negatively charged phage capsid followed by PBSE-based covalent linkage, leading to oriented immobilization and higher bacteria capture efficiency. As a result, the electric field-induced, charge directed immobilization of phage particles could in turn affect the overall biosensor sensitivity.

Figure 9:
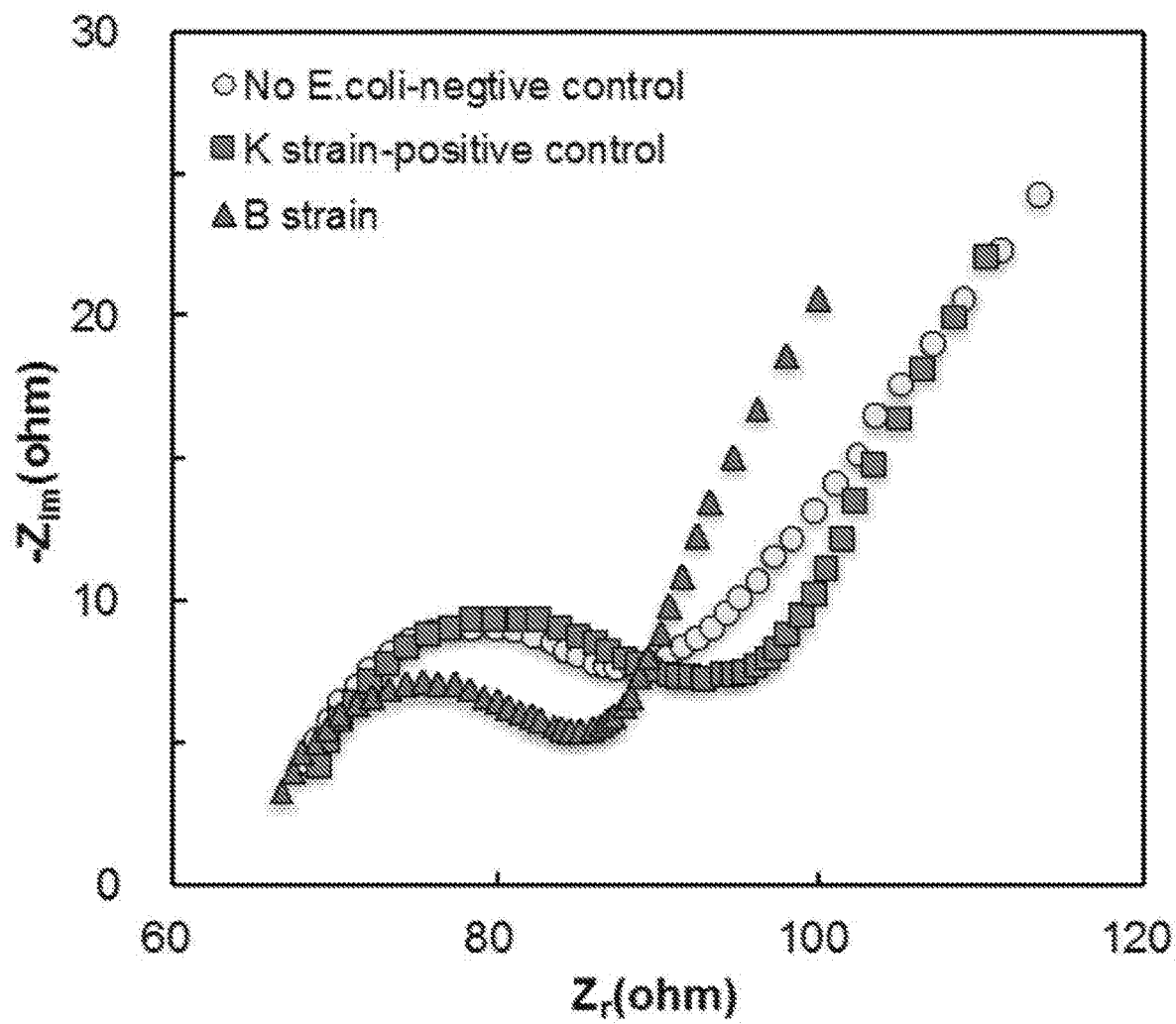
FIG. 9 shows Nyquist plots of a T2 page-modified electrode for the detection of *E. coli* K strain.

To evaluate the specificity of the T2 phage towards the B strain of $E.$ $coli$, the biosensor was tested using non-host control bacteria $E.$ $coli$ K strain (at $10^6$ CFU/mL, FIG. 8). No plaques were observed after T2 phage incubation with K strain $E.$ $coli$ (data not shown). FIG. 9 shows the Nyquist plots of T2 phage-modified electrodes used for capturing $E.$ $coli$ K strain. There was no significant variation in the impedance spectra of the phage-modified electrode before and after exposure to $E.$ $coli$ K strain. After fitting the Nyquist results into Randles equivalent circuit, a slightly increase in $R_{CT}$ was observed from 18.7Ω to 19.4Ω; however, comparing with $E.$ $coli$ B strain with same bacteria concentration, $R_{CT}$ underwent dramatic decrease after cell attachment. The results demonstrate that the phage-biosensor is highly specific only to the target host organisms, whereas the K strain only interacts with surface immobilized phages through physical adsorption.

Conclusion

The present example demonstrated a new approach for whole cell bacteria detection using bacteriophage-assisted CNT-based electrochemical biosensor. A reliable charged-directed immobilization of bacteriophages on CNT was developed by combining electric field-induced immobilization and covalent crosslinking. Bacteriophage particles were deposited with tail-out and capsid-in orientation, followed by covalent binding onto PEI-functionalized CNT sidewall through molecular crosslinkers. This new approach offers a high loading of bio-recognition molecule on the transducer surface, which in turn results in increased sensitivity of the biosensor. The immobilized phage particles retained their high infectivity towards host bacteria cells as confirmed by fluorescence microscopy. The biosensor was highly selective towards $E.$ $coli$ B strain with a reliable detection limit of $10^3$ CFU/mL. Future studies will also focus on improving the performance of the biosensor by extending phage deposition time and increasing substrate surface area to obtain higher surface coverage of phages. Meanwhile, a homogeneous electrode surface, for example, electrode with CNT directly grown on the surface, will definitely be helpful for uniform surface electric field-induced immobilization, leading to oriented phage immobilization with minimal particle aggregation. The charge-directed immobilization method for bacteriophage attachment on CNT that has been developed in this work could be widely applied for the developing of other type of biosensors and biological electrodes.

Example 2—Phage-Assisted Sample Enrichment

At present, the predominant methods for detecting food pathogens are traditional microbiological and biochemical procedures such as colony counting, polymerase chain reaction (PCR) or enzyme-linked immunosorbent assay (ELISA) that typically take up to 48 hours to a few days depending on the nature of the sample. These tedious procedures are further complicated by the long sample pretreatment (enrichment) procedures that last 10-24 h or more, causing a significant time lag between the first outbreak of disease to its identification and verification. To overcome this, a variety of rapid detection biosensors have been developed for detecting food pathogens with varying degree of success. But, the time-consuming sample enrichment procedures for these biosensors limit the duration of food pathogen screening tests. There is thus a pressing need to develop a method that combines rapid sample enrichment and rapid detection in a single step/method/platform that could enable the development of 'true' lab-on-chip devices. Such a method or device that could perform both isolation/enrichment (of pathogens from food matrix) and detection within a short period (~1 h) does not currently exist. The present example provides a method for detection of *Listeria* species in real food samples by combining rapid enrichment and selective electrochemical detection using bacteriophage. The methods and results below demonstrate isolation and detection of *Listeria monocytogenes* from complex food matrices that could also be extended to other applications.

Background

Among the food pathogens, *Listeria monocytogenes* is deadly with a high fatality rate (>15%), and listeriosis disease (caused by *L. monocytogenes*) is the 3rd leading cause of death from food poisoning, costing $2.7 billion annually to the U.S. healthcare. The pathogenic microbe is often found in uncooked foods such as meat, raw milk, cheese and vegetables. Table 2.1 lists the commercially available test kits for *Listeria* spp.

ment process (up to 48 h), rendering any rapid detection capability of the biosensor useless. Fast magnetic bead-based enrichment methods have been developed for conventional microbiological or biochemical methods[17, 32-40], but have rarely been used for biosensors[41].

Ideally, a food pathogen-screening test would combine rapid enrichment with rapid detection with no trade-off in selectivity, sensitivity and detection limits. The only commercial biosensor for *Listeria* (Detect/L, Sample6.com) was developed by Lu and Koeris at MIT[42]. The test takes 6 hours to complete through a series of 5 steps from sample collection to detection, while also requiring an incubator and centrifuge in addition to an optical detector. Based on their earlier reports[42, 43], it could be understood that their synthetic biology-based method involves infecting *Listeria* cells with a fluorescence-tagged bacteriophage and allowing it to propagate through one or more lytic cycles in order to "light up" the target pathogen for optical detection. Six hours is, by far, the shortest duration achieved for *Listeria* spp test. However, present example describes a system to reduce this duration by at least 5 fold to less than 1 hour and the number of required instruments to just a single, integrated unit.

The present approach involves recombinant engineering, interfacial science, and electrochemistry to provide a bacteriophage-assisted, viro-magnetic enrichment and selective detection method for rapid identification and quantification of *L. monocytogenes* in complex food matrices.

Experimental Results

Figure 10:
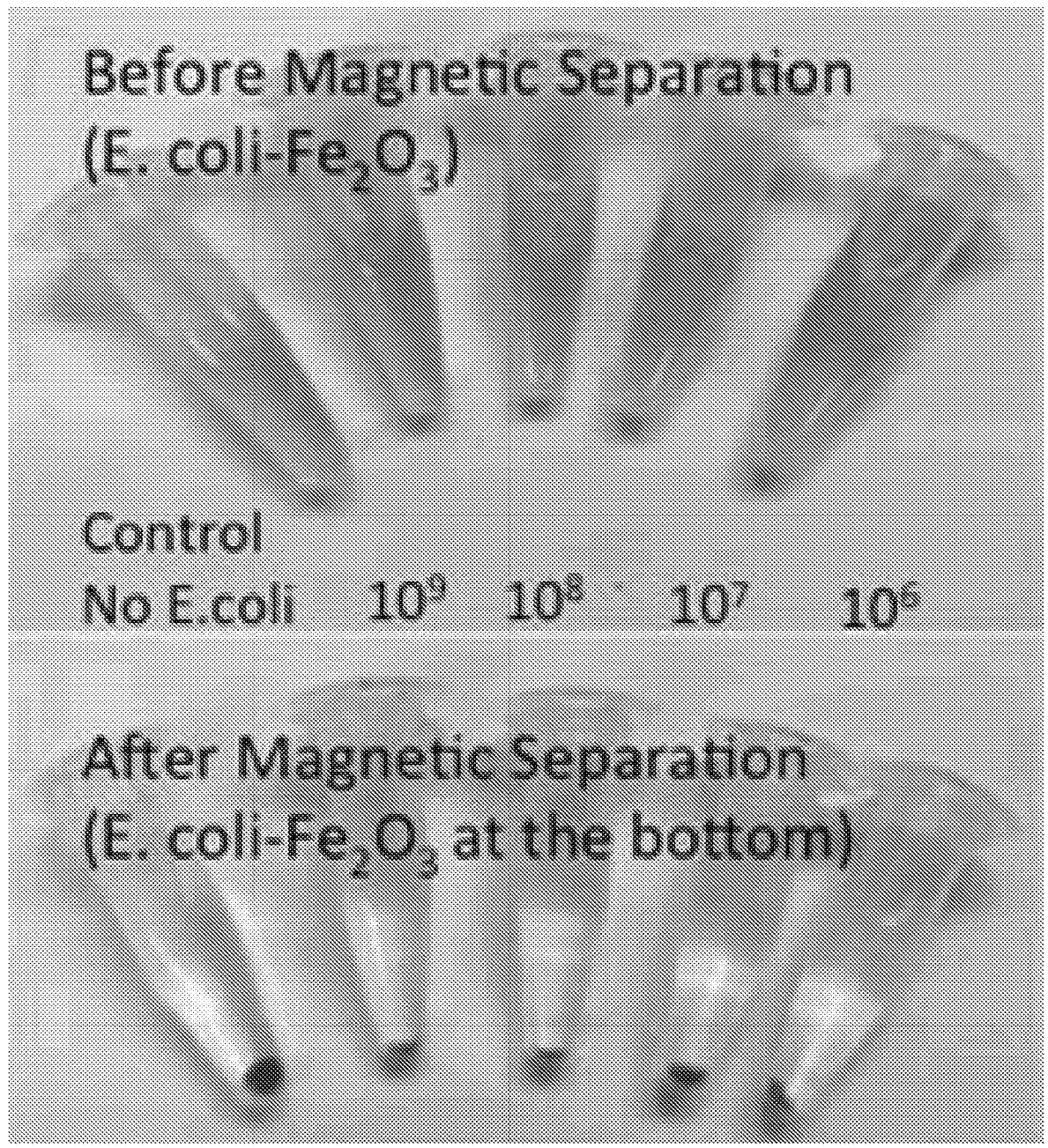
FIG. 10 shows digital images illustrating magnetic separation of *E. coli* cells from solution using non-functionalized $Fe_2O_3$ microbeads.

Isolation of *E. coli* Using $Fe_2O_3$ Super Paramagnetic Micro-Beads:

*E. coli* cells were isolated from a sample using $Fe_2O_3$ super paramagnetic microbeads. Preliminary results suggest that about 85-90% of bacterial cells could be separated using a magnet even without surface functionalization of $Fe_2O_3$. The $Fe_2O_3$ microbeads form P—OFe bonds with the phospholipid rich *E. coli* cell membrane[46, 47], which aids in $Fe_2O_3$ attachment and magnetic separation. Initial magnetic separation is illustrated in FIG. 10.

Production of P100 Phage-Modified SPMNP for Binding *Listeria*:

The present example further demonstrates immobilization of the P100 bacteriophage on super paramagnetic nanoparticles (SPMNP). Such phage-modified nanoparticles can be used to selectively bind to *Listeria* cells in food samples and isolate the SPMNP bound *Listeria* cells with the help of a simple magnet.

TABLE 2.1

Commercially available *Listeria* kits.

| Commercial Kit | Sample Enrichment | Method of Identification | Total Duration | Positive Control | USDA Approved |
| --- | --- | --- | --- | --- | --- |
| MICRO-ID Listeria | Agar culture | Colorimetric | ~24 h. + 24 h. | Yes | Yes |
| API *Listeria* | Agar culture | rRNA tests | 18-24 h. + 4 h. | Yes | Yes |
| VITEK 2 | Unknown | Colorimetric | Unknown + 8 h. | Unknown | Yes |
| Microbact Listeria | Agar culture | Colorimetric | 24 h. + 4 h. + 24 h. | Unknown | No |
| MicroSEQ | Unspecified | Real-time PCR | 4 h. + 3 h. | Unknown | No |
| OLRT, Oxoid | Agar culture | ELISA (antigen based) | 42-52 h. + 1 h. | Yes | No |
| Detect/L, Sample 6 | Unknown | Biosensor (Optical) | 6 h. | No | Yes |

Figure 11:
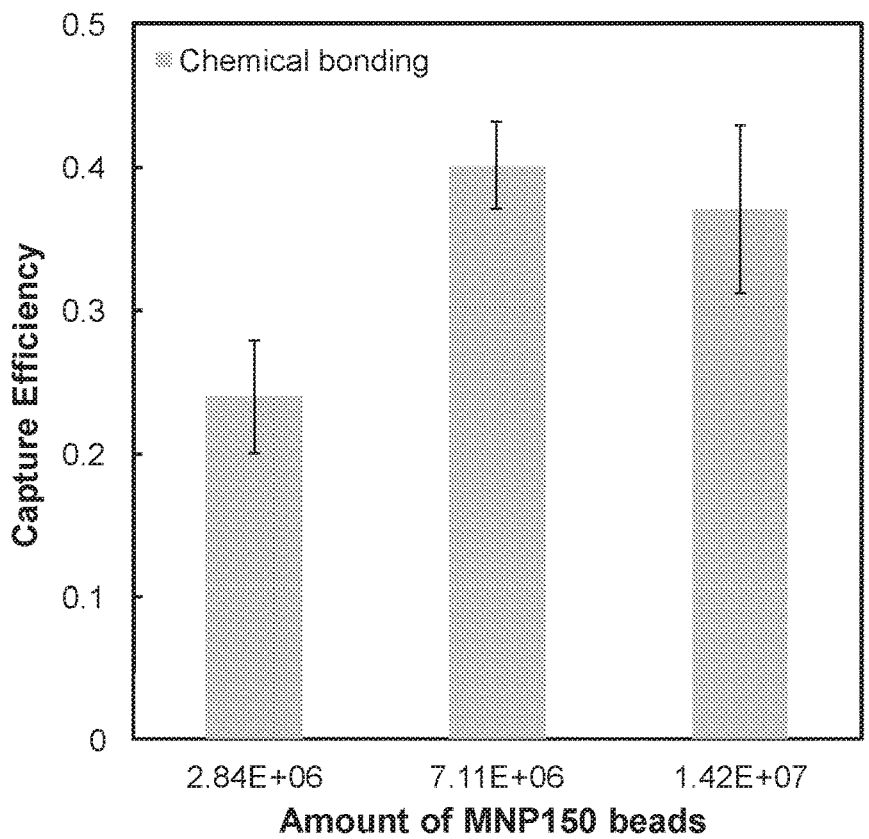
FIG. 11 is a bar graph illustrating *Listeria monocytogenes* capture efficiency by different quantities of MNP150 magnetic nanoparticles (150 nm in diameter) chemically bonded to P100 phage particles.
Figure 12:
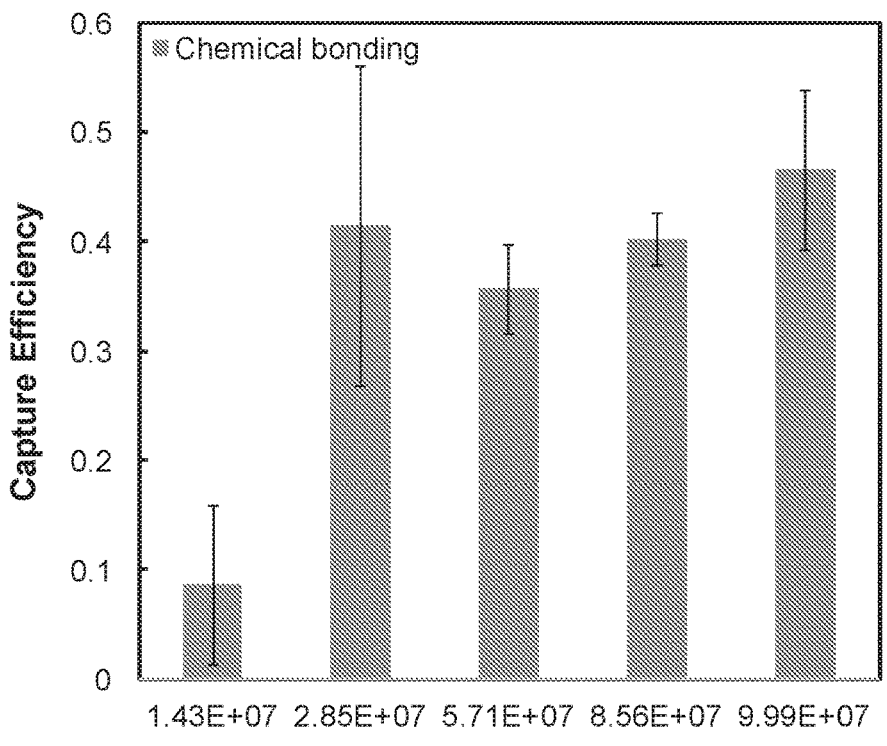
FIG. 12 is a bar graph illustrating *Listeria monocytogenes* capture efficiency by different quantities of MNP500 magnetic nanoparticles (500 nm in diameter) chemically bonded to P100 phage particles.

Clearly, the existing molecular methods for *listeria* identification are time consuming, require laboratory set-up, and require skilled experts to analyze the results. While biosensors offer a quicker solution, a bottleneck of using biosensors for food pathogen screening is the slow sample enrich- Phage were successfully immobilized onto MNP 150/MNP500 through chemical bonding. The effect of the MNP150/MNP500 quantity on the capture efficiency for *L. monocytogenes* was examined by adding various amount of MNP150/MNP500 to cell suspension with a concentration of $10^2$ CFU/mL. Results are illustrated in FIGS. 11 and 12. As shown in the figures, the capture efficiency increases and levels off at higher MNP counts.

Example 2 References

17. Shihabi, Z. K.; Deyl, Z., Preconcentration and sample enrichment techniques—Preface. J Chromatogr A 2000, 902, 1-1.
32. Fratamico, P. M.; Schultz, F. J.; Buchanan, R. L., Rapid Isolation of *Escherichia-Coli* O157-H7 from Enrichment Cultures of Foods Using an Immunomagnetic Separation Method. Food Microbiol 1992, 9, 105-113.
33. Mansfield, L. P.; Forsythe, S. J., Immunomagnetic Separation as an Alternative to Enrichment Broths for *Salmonella* Detection. Letters in Applied Microbiology 1993, 16, 122-125.
34. Partridge, M.; Phillips, E.; Francis, R.; Li, S. R., Immunomagnetic separation for enrichment and sensitive detection of disseminated tumour cells in patients with head and neck SCC. J Pathol 1999, 189, 368-377.
35. Steingroewer, J.; Knaus, H.; Bley, T.; Boschke, E., A rapid method for the pre-enrichment and detection of *Salmonella typhimurium* by immunomagnetic separation and subsequent fluorescence microscopical techniques. Eng Life Sci 2005, 5, 267-272.
36. Finlay, D.; Bell, C.; Ball, H. J., Comparison of a monoclonal antibody-based capture/enrichment sandwich enzyme linked immunosorbent assay with immunomagnetic bead separation for the detection of attachment effacement *Escherichia coli* O26 strains from cattle faeces. Journal of Applied Microbiology 2006, 100, 1141-1146.
37. Himathongkham, S.; Dodd, M. L.; Yee, J. K.: Lau, D. K.; Bryant, R. G.: Badoiu, A. S.; Lau, H. K.; Guthertz, L. S.; Crawford-Miksza, L.; Soliman, M. A., Recirculating Immunomagnetic separation and optimal enrichment conditions for enhanced detection and recovery of low levels of *Escherichia coli* O157: H7 from fresh leafy produce and surface water. J Food Protect 2007, 70, 2717-2724.
38. Wang, Z. L.; Yue, T. L.; Yuan, Y. H.; Cai, R.; Niu, C.; Guo, C. X., Preparation of immunomagnetic nanoparticles for the separation and enrichment of *Alicyclobacillus* spp. in apple juice. Food Res Int 2013, 54, 302-310.
39. Xiong, Q. R.; Cui, X.; Saini, J. K.; Liu, D. F.; Shan, S.; Jin, Y.; Lai, W. H., Development of an immunomagnetic separation method for efficient enrichment of *Escherichia coli* O157:H7. Food Control 2014, 37, 41-45.
40. Zhan, S.; Yang, Y.; Shen, Z.; Shan, J.; Li, Y.; Yang, S.; Zhu, D., Efficient removal of pathogenic bacteria and viruses by multifunctional amine-modified magnetic nanoparticles. J. Hazard. Mater. 2014, 274, 115-23.
42. Lu, T. K.; Bowers, J.; Koeris, M. S., Advancing bacteriophage-based microbial diagnostics with synthetic biology. Trends Biotechnol 2013, 31, 325-327.
43. Lu, T.; Koeris, M. S.; Holder, J.; McKenzie, G.; Brownell, D. Recombinant Phage and Methods. US 2013/0122549 A1, 2013.
46. Cagnasso, M.; Boero, V.; Franchini, M. A.; Chorover, J., ATR-FTIR studies of phospholipid vesicle interactions with alpha-FeOOH and alpha-$Fe_2O_3$ surfaces. Colloid Surface B 2010, 76, 456-467.
47. Parikh, S. J.; Chorover, J., ATR-FTIR spectroscopy reveals bond formation during bacterial adhesion to iron oxide. Langmuir 2006, 22, 8492-8500.

Example 3

Introduction

*Listeria monocytogenes* is a food-borne pathogen frequently found in frozen vegetables, meat, raw milk, packaged salad and raw milk cheese that causes severe foodborne illnesses. It has one of the highest fatality rates among common food-borne pathogens. *L. monocytogenes* could grow over a wide temperature range from −0.4 to 45° C., under both aerobic and anaerobic conditions and over a wide pH range. Due to its high tolerance for harsh environments, *L. monocytogenes* could contaminate food at any of the multiple points in the food processing chain. The FDA allowable limits for *Listeria monocytogenes* contamination in ready-to-eat (RTE) food products is <1 CFU/25 g of food that supports the growth of *L. monocytogenes* and 100 CFU/g of food that do not support its growth.

Conventional methods for identification of *Listeria* in food matrices include plating on selective and differential agar and/or biological and serological confirmation. These methods of identification require separate pre-concentration or enrichment step(s) in order to collect sufficient quantity of bacterial cells to enable a reliable identification. Moreover, during the enrichment process, nonpathogenic species may compete and outgrow *L. monocytogenes*, which could lead to false-negative results during identification. While being reliable and accurate, traditional methods are also time-consuming and need well-trained operators to conduct the experiment. Therefore, it would be beneficial to develop new analytical methods that help in rapid and reliable identification of *Listeria* in food samples.

In recent years, immunomagnetic separation (IMS) has been widely used in the pathology labs for separation and identification of target bacteria from different food. In IMS, mono-clonal antibodies are used as recognition elements that are immobilized onto magnetic particle surfaces for bacterial cell separation in the presence of a magnetic field. IMS could significantly shorten enrichment time, and improve the sensitivity of detection, but it is prone to false positive identification through non-specific interactions between non-target cells and magnetic particles. Moreover, antibodies used in IMS are typically expensive, as well as susceptible to pH and temperature variations making them less suitable for non-laboratory testing. Commercially available 2.8 μm Dynabeads coupled with polyclonal antibodies may be capable of separating target bacterial cells but with a low capture efficiency generally (7-23%).[1,9,10] Therefore, improved methods for bacterial cell isolation/enrichment/separation of *Listeria* from complex food matrices would be advantageous in order to enable rapid screening of *Listeria* in food samples.

Similar to antibodies, bacteriophages offer high selectivity toward their host bacteria and could discriminate between viable cells and dead cells.[11] In addition, phages are inexpensive, ubiquitous in the nature and possess robust stability under sub-optimal conditions. A phage could recognize the target bacteria through the receptors located on bacterial cell surface. Upon host recognition, the phage selectively binds to the bacterial cell wall. The genetic material of phage is then injected into the bacterial cell, which initiates protein synthesis, phage assembly and replication. The high selectivity of bacteriophage towards its host could be utilized for bacterial cell isolation and enrichment from food samples as an alternative to antibody based bacterial separation methods.[12-16] The United States Department of Agriculture (USDA) has approved two bacteriophages for *L. monocytogenes* control in foods: LISTEX™

P100 and LMP-102.[17-19] Phage-based magnetic separation of *Salmonella* cells from food samples has been previously reported.[20] However, there is very little information in the literature about the importance of phage immobilization methods on the effectiveness of phage coupling with magnetic particles, retention of phage's infectivity after immobilization and the bacterial cell capture efficiency[21-24].

The present example addresses major knowledge gaps in this area. This example describes an experimental study on the use of bacteriophage P100 as a model bio-receptor to study phage immobilization on magnetic particles for separation and isolation of *L. monocytogenes* from food matrices. The present example also describes the effect of phage immobilization methods and the size of magnetic particles on the effectiveness of phage attachment (coupling) to the magnetic beads and its bacterial cell capture efficiency. Three different sizes of magnetic particles (150 nm, 500 nm and 1 μm) and two different phage immobilization methods (physical and chemical) were investigated. In many literatures, covalent chemical immobilization method is commonly adopted for phage immobilization. However, very few studies have reported the importance of phage immobilization methods on the effectiveness of phage coupling with magnetic particles.[20,24] Upon immobilization, the P100 phage-modified magnetic particles (PMMP) were used for *L. monocytogenes* separation from dilute *Listeria* contaminated buffer solutions and the resulting capture efficiency were investigated. The PMMP were also used for selective isolation of *L. monocytogenes* from whole milk and ground beef samples to demonstrate their suitability for field applications in food industry.

Material and Methods

Materials and Instruments

The following chemicals were purchased and used without further purification: sodium chloride and sodium phosphate dibasic (both from EMD chemicals, Port Wentworth, Ga.), potassium chloride (J.T. Baker, Center Valley, Pa.), potassium dihydrogen phosphate (BDH, West Chester, Pa.), magnesium sulfate heptahydrate (J.T. Baker, Center Valley, Pa.), agar powder (Alfa Aesar, Ward Hill, Mass.), bis(sulfosuccinimidyl)suberate) (BS3) (Cova Chem, Loves Park, Ill.), Tris-HCl (Fisher Scientific, Fair Lawn, N.J.), Brain heart infusion medium (Sigma-Aldrich, St. Louis, Mo.) SM buffer was prepared by mixing 5.8 g of NaCl, 2 g of $MgSO_4 \cdot 7H_2O$, 50 mL of 1M Tris-HCl pH 7.5, and 1 mL of 10% (w/v) gelatin in deionized water. Brain heart infusion (BHI) medium was prepared by adding 37 g of BHI powder in deionized water and adjusted to pH 7.4. BHI-agar medium was prepared by adding 6 g of agar to 400 mL of BHI media. 2 g of agar was added to 400 mL of BHI media to obtain soft agar medium. 10× phosphate buffered saline (PBS) was prepared by mixing 16 g NaCl, 0.40 g KCl, 2.8 g $Na_2HPO_4$, and 0.49 g $KH_2PO_4$ in 200 mL deionized water yielding a buffer solution of pH 7.4. The prepared PBS was further diluted to 1× before use. All media, buffer and glassware were sterilized before use. *Listeria monocytogenes* Scott A strain was kindly provided by University of Georgia, Griffin. P100 bacteriophage (commercial name LISTEX™) was purchased from Micreos Food Safety (Wageningen, The Netherlands). The amine functionalized magnetic beads of 150 nm, 500 nm, and 1 μm size were purchased from Ocean Nanotech (Springdale, Ark.). The magnetic separation of the particles during the washing steps were carried out using a magnetic separation rack (Bel-Art, Wayne, N.J.). A tube rotator (VWR, Suwanee, Ga.) was used for mixing steps at a speed of 18 rpm.

Bacterial Strains and Culture Conditions

*Listeria monocytogenes* Scott A was used throughout the separation experiments unless otherwise stated. *L. monocytogenes* was cultured in 4 mL BHI medium overnight at 37° C. 500 μL aliquot of the overnight culture was inoculated into 50 mL of fresh BHI medium by shaking at 200 rpm for 5 h at 37° C. in an incubator shaker. 1 mL of the bacteria culture was transferred into 1.5 mL centrifuge tube and the cell suspension was centrifuged at 4000 g for 10 min. The supernatant was removed and bacterial cell pellet was resuspended with 1×PBS buffer and washed twice before each separation experiment. Enumeration of bacteria was performed by plate counting method and cell count was expressed in CFU/mL. All other bacterial strains were grown in LB medium using similar growth conditions as described above.

Preparation of Bacteriophage-Functionalized Magnetic Particles

Figure 13A:
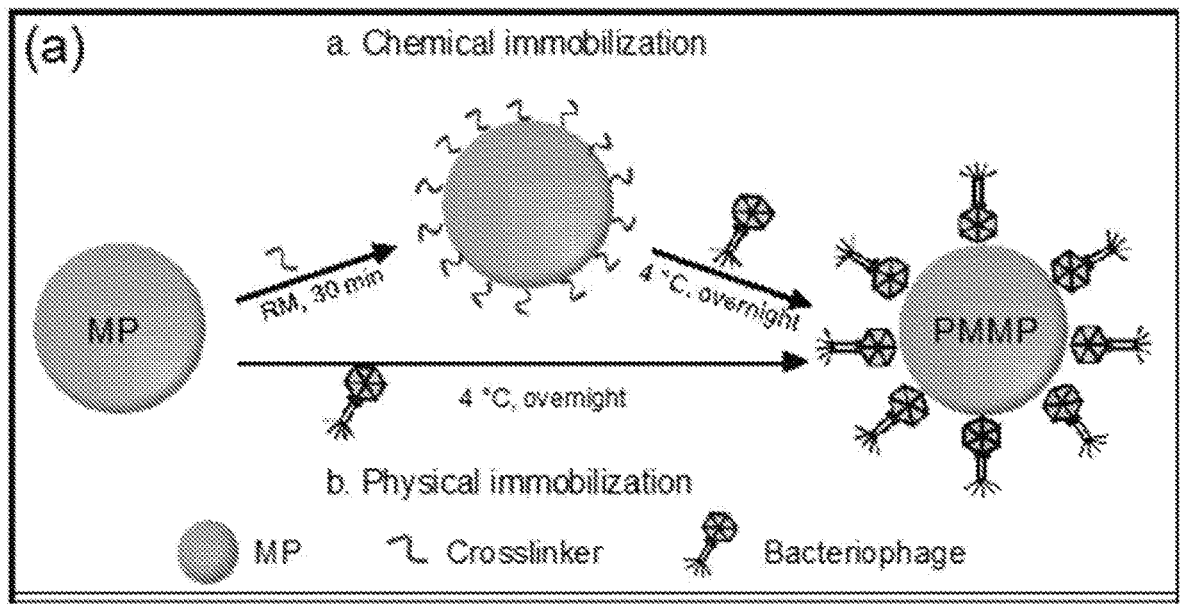
FIG. 13A is an example of MP modification with bacteriophage via chemical and physical immobilization methods.

Three different sizes of amine functionalized magnetic particles (MP) were used for phage immobilization: 150 nm, 500 nm and 1 μm. 20 μL of MP (10 mg/mL) was aliquoted and added into a 1.5 mL micro-centrifuge tube. Followed by sterilizing the particles with 70% ethanol, the tube was placed on a magnetic separator to remove the ethanol. The particles were washed three times using 1×PBS buffer (coupled with 0.01% Tween 20). PBS buffer was then added into the tube to form a suspension of MP. As depicted in FIG. 13A, phages were immobilized onto MP surface via two methods. The chemical immobilization of phages was achieved using bis(sulfosuccinimidyl)suberate) (BS3) cross-linker, which reacts with the surface amine moieties of phage particles resulting in amide bond formation. In physical immobilization method, the immobilization of phage particles was mainly driven by Van der Waals and electrostatic interactions.[25,26]

For the preparation of chemical immobilization of phages onto MP surface, 10 mM of BS3 in PBS was prepared, syringe-filtered and added into the MP suspension. The mixture of BS3 and MP were reacted for 30 minutes at room temperature with continuous mixing using the tube rotator to allow the activation of MP surfaces. After 30 minutes, the tube was placed into the magnetic separator for activated MP separation. The particles were then washed three times with 500 μL of PBS buffer to remove excess BS3 and then re-suspended in 400 μL PBS buffer. Finally, phage particles ($10^8$ or $10^9$ PFU) were added into the MP suspension to react overnight at 4° C. under continuous mixing at 18 rpm using tube rotator. The prepared phage-modified MP (PMMP) was then magnetically separated and washed three times with PBS buffer. The supernatant was removed and placed in another tube to perform plaque assay, in order to determine the free phage quantity in the supernatant. The PMMP were resuspended in 500 μL SM buffer and incubated for two hours at 4° C. under continuous mixing to terminate the excess surface activated residuals. The thus-prepared phage chemically functionalized MP of different sizes were designated as PMMP-150Ch, PMMP-500Ch and PMMP-1000Ch, respectively.

For physical immobilization, no pre-activation of MP surfaces was needed. Phage particles were directly added into sterilized MP suspension to react overnight at 4° C. under continuous mixing at 18 rpm using tube rotator. The phage-modified MP were then washed three time with PBS buffer. The supernatant was also obtained for plaque assay study. Excess surface activated residue was terminated using SM buffer as mentioned previously. The thus-modified MP were noted as PMMP-150Ph, PMMP-500Ph and PMMP- 1000Ph, respectively. The phage-modified MP (PMMP) were finally stored at 4° C. for later use in bacterial cell separation experiments. Plaque assay was used to determine the phage quantity and infectivity of PMMP in the collected supernatant. Briefly, the obtained collected supernatant sample was serially diluted with 1×PBS buffer and added to a test tube containing 3 mL molten soft agar (0.5%) with 250 µL of L. monocytogenes culture. The solution was poured over BHI agar plate and incubated overnight at 30° C. The visible plaques were counted the following day. The initial phage quantity was also determined using plaque assay before each experiment. The remaining phage quantity in the supernatant was then compared with the initial phage quantity in order to calculate the phage coupling ratio (CR) of PMMP, which is defined as follows: $CR=1-C_S/C_I$, where $C_S$ is the number of free phages remaining in the supernatant after separation and $C_I$ is the initial number of phages used for immobilization. Data were collected from three independent experiments were analyzed in duplicate unless otherwise stated.

Bacterial Capture Efficiency Determination

Figure 13B:
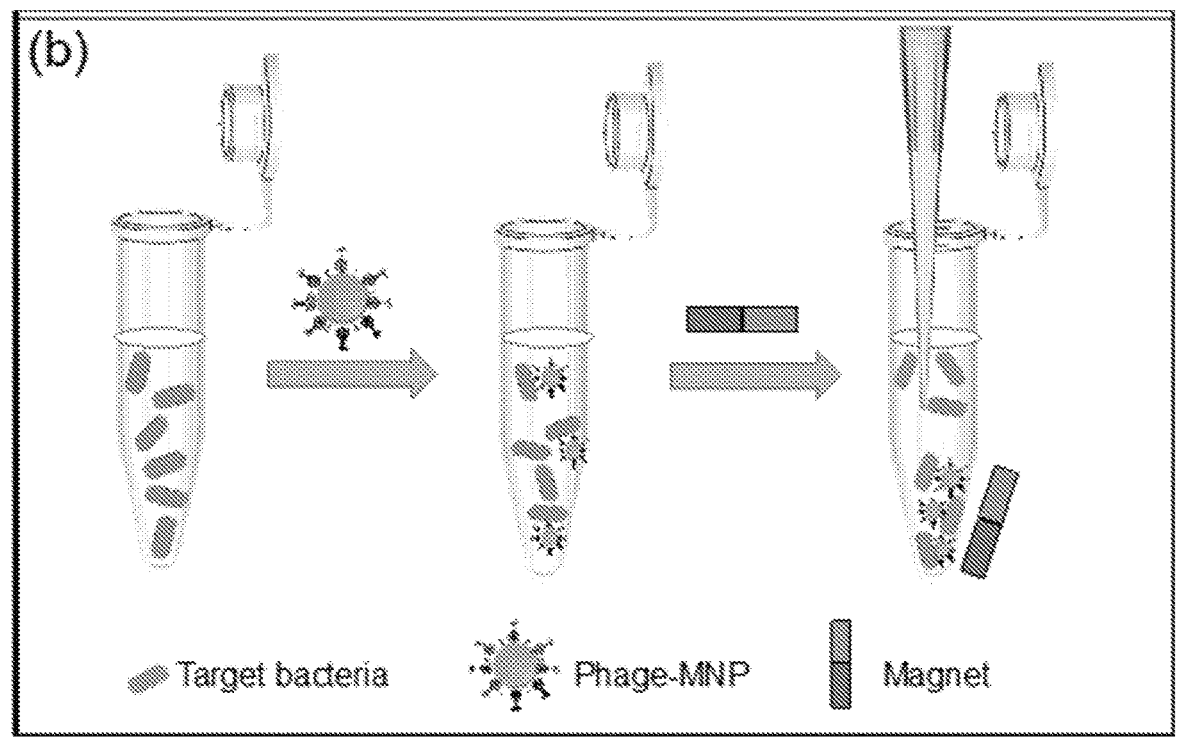
FIG. 13B is an example of magnetic separation of *Listeria. monocytogenes* captured on PMMP from bacterial suspension.

Bacterial cell separation was performed using 500 µL of bacterial cell suspension in micro-centrifuge tubes. The process of separation was illustrated in FIG. 13B. L. monocytogenes cells were serial diluted to make $10^2$ to $10^6$ CFU/mL cell suspension in PBS buffer, as confirmed with plate counting technique. Subsequently, different volumes of the 0.4 mg/mL functionalized magnetic particles (20 µL, 40 µL, 80 µL, 120 µL, and 140 µL) were added to the sample and incubated at room temperature for 10 min without agitation, and then for 5 min with rotation using tube rotator. The MP-bacteria complex was then separated using a magnetic separator over a period of 5 min. The supernatant was collected and plated on BHI agar plates which were then incubated at 37° C. for 24 to 48 hours for quantification. The initial L. monocytogenes cells were also plate-counted in order to calculate the number of captured cells. The capture efficiency (CE) was then calculated using the formula: $CE(\%)=(1-C_S/C_I)\times 100$, where $C_S$ is the number of L. monocytogenes cells remaining in the supernatant after separation and $C_I$ is the initial total number of L. monocytogenes cells in the sample.

Microscopy Characterization

The capture ability of PMMP was qualitatively observed using scanning electron microscopy. Each PMMP sample of 80 µL was added into 500 µL L. monocytogenes cell suspension of $10^6$ CFU/mL for bacterial capture. The mixture was incubated at room temperature for 10 min without agitation and then for 5 min with rotation using tube rotator. After that, the MP with attached bacteria were washed with PBST(×3), and then re-suspended in sterilized water. The resulting suspension was then filtered through a Nucleopore membrane (13 mm Ø, 0.1 µm/0.2 µm pore size). The filters were pre-fixed using 3% glutaraldehyde in pH 7.4 phosphate buffer for overnight at 4° C., and post-fixed with osmium tetroxide for 2 h. After fixation, the samples were rinsed and dehydrated with ethanol gradient. Samples were then mounted on metallic stubs with adhesive carbon tapes and sputtered with gold for 30 s before scanning microscopy observation.

The capture ability of PMMP were also characterized using fluorescence microscopy. PMMP (1 µm) suspension was added into 500 µL SYBR gold labeled L. monocytogenes sample for cell separation, followed by the separation process as previously mentioned. After that, the PMMP with attached bacteria were washed with PBS(×3), and then resuspended in PBS buffer. A single drop of the resulting suspension on a glass slide was examined using fluorescence microscopy.

Selectivity and Stability Study

The selectivity of the PMMP towards L. monocytogenes was evaluated using other non-target bacterial strains such as Escherichia coli B (ATCC 11303), Staphylococcus aureus (ATCC 6538), and Enterococcus faecalis, provided by Dr. Hitesh Handa (University of Georgia, Athens). Each bacteria strain was cultured in LB medium at 37° C. and then serial diluted to $10^4$ CFU/mL in PBS buffer. L. monocytogenes was also cultivated to a final concentration of $10^4$ CFU/mL. Any binding of PMMP to non-target bacteria was tested by plate counting method as described above in order to determine the selectivity of the phage-MP towards L. monocytogenes.

The long-term stability of the phage-modified MP was evaluated by monitoring the activity of PMMP using plaque assay. For this purpose, phage-MP complexes were prepared with 1 µm magnetic particles using both physical and chemical functionalization methods. The prepared PMMP-1000Ch and PMMP-1000Ph were stored at 4° C. in SM buffer, and intermittently warmed to room temperature before use in stability tests. Data were collected from three independent experiments were analyzed in duplicate and the mean values were obtained and compared with the initial activity of PMMP to determine the stability.

Capture of L. monocytogenes from Contaminated Food Samples

In order to evaluate the capture of L. monocytogenes by PMMP from real food samples, whole milk and ground beef purchased from local grocery store were used as the food matrix for bacteria growth. For this test, 25 g of whole milk or beef was spiked with Listeria monocytogenes in 225 mL of PBS buffer to make the stock food sample ($10^3$ CFU/mL). Both PMMP-1000Ch and PMMP-1000Ph were tested for L. monocytogenes separation and 80 µL of either was added to 500 µL of stock food sample. The mixture was incubated for 10 min without agitation and then for 5 min with rotation of 18 rpm. The supernatant was then serial-diluted and plated for bacterial cell counting. Data were collected for three individual experiments performed in duplicates.

Results and Discussion

Immobilization of Bacteriophage on Magnetic Particles

As depicted in FIG. 13A, P100 phages were immobilized onto magnetic particle surfaces through two immobilization methods: covalent chemical immobilization and physical immobilization. Plaque assay was performed using the collected supernatant and the phage coupling ratio (CR) was used as a parameter to determine the effectiveness of phage immobilization on MP. The CR of P100 phage binding on to MP could be influenced by several ratios, including type of immobilization method, phage quantity in sample and MP size. The influence of these on phage-magnetic particle CR is summarized in Table 3.1. Firstly, the influence of immobilization method on phage CR was studied by immobilizing $10^8$ PFU phages onto MP surfaces using both chemical and physical immobilization methods. CR obtained from chemical immobilization of phages is higher than that obtained from physical immobilization of phages. For example, the CR of PMMP-150Ph is 0.46 and the CR of PMMP-150Ch is 0.43. This effect was also observed for 500 nm and 1 µm sized MP.

Secondly, the influence of phage quantity on CR was studied by using $10^8$ and $10^9$ PFU (in 0.4 mL) of phages for immobilization on MP surface. When high quantity of phages ($10^9$ PFU) was employed for phage chemical immobilization on small MP, the CR of PMMP-150Ch increased from 0.46 to 0.6. However, for the medium sized MP, the CR of PMMP-500Ch decreased from 0.61 to 0.27 and for the large sized MP (1 μm), increasing phage quantity did not translate into increased CR as well. The results suggest that MP size is an important parameter that determines the P100-MP coupling ratio and the resulting surface phage loading of P100 onto MP. The high CR of small MP (150 nm) over medium and larger MP could be attributed to the high surface/volume ratio and high mobility of small particles that could provide more opportunity to interact with phages.

TABLE 3.1

Phage-magnetic particle coupling ratios of three different sizes of magnetic particles using chemical/physical immobilization method.
Phage-magnetic particle coupling ratio

| Phage quantity | 150Ch | 150Ph | 500Ch | 500Ph | 1000Ch | 1000Ph |
|---|---|---|---|---|---|---|
| $10^8$ PFU | 0.46 | 0.43 | 0.61 | 0.18 | 0.25 | 0.19 |
| $10^9$ PFU | 0.60 | 0.61 | 0.27 | 0.27 | 0.27 | 0.18 |

Retention of Phage Infectivity in PMMP

The infectivity of each PMMP was also studied to further establish the effectiveness of phage immobilization methods. Each PMMP was directly examined using plaque assay and the immobilized plaque quantity was obtained. The total plaque quantity could help to understand the overall lytic activity, which was defined as immobilized phage quantity/MP number. As shown in Table 3.2, PMMP prepared with $10^9$ PFU phages achieved 1-2 orders of magnitude higher lytic activity than that of PMMP prepared with $10^8$ PFU phages. The increase of phage quantity improved the overall lytic activity of each PMMP. Besides high P100-MP coupling ratios, the smaller 150 nm MP exhibited very low lytic activity (0.001% and 0.01%), whereas medium (500 nm) and large (1 μm) PMMP showed 2-3 orders of magnitude higher lytic activity than small particle. These results are not in direct agreement with results of CR for 150 nm MP (40-60%) as mentioned previously. A high CR for 150 nm PMMP did not translate into a high PMMP lytic activity. This could due to high particle agglomeration for small MP that occurred during surface activation and phage immobilization. Moreover, the overall lytic activity of PMMP with chemically immobilized phages was lower than that of PMMP with physically immobilized phages. Such variance in lytic activity was consistent with the obtained CR of two the immobilization methods. Given the fact that only phages with preferred orientation (e.g. head-in, tail-out fashion) could produce a plaque of the PMMP, the overall low lytic activity of MP with chemically immobilized phages could be the result of random immobilization of phages on MP surfaces, such as tail-in, head-out fashion.

TABLE 3.2

Lytic activity of each PMMP of three different sizes of magnetic particles using chemical/physical immobilization method.
Lytic activity (%)

| Phage quantity | 150Ch | 150Ph | 500Ch | 500Ph | 1000Ch | 1000Ph |
|---|---|---|---|---|---|---|
| $10^8$ PFU | 0.001 | 0.01 | 0.01 | 0.1 | 0.1 | 0.1 |
| $10^9$ PFU | 0.01 | 0.1 | 0.1 | 1 | 1 | 1 |

*L. monocytogenes* Separation with PMMP

Figure 14:
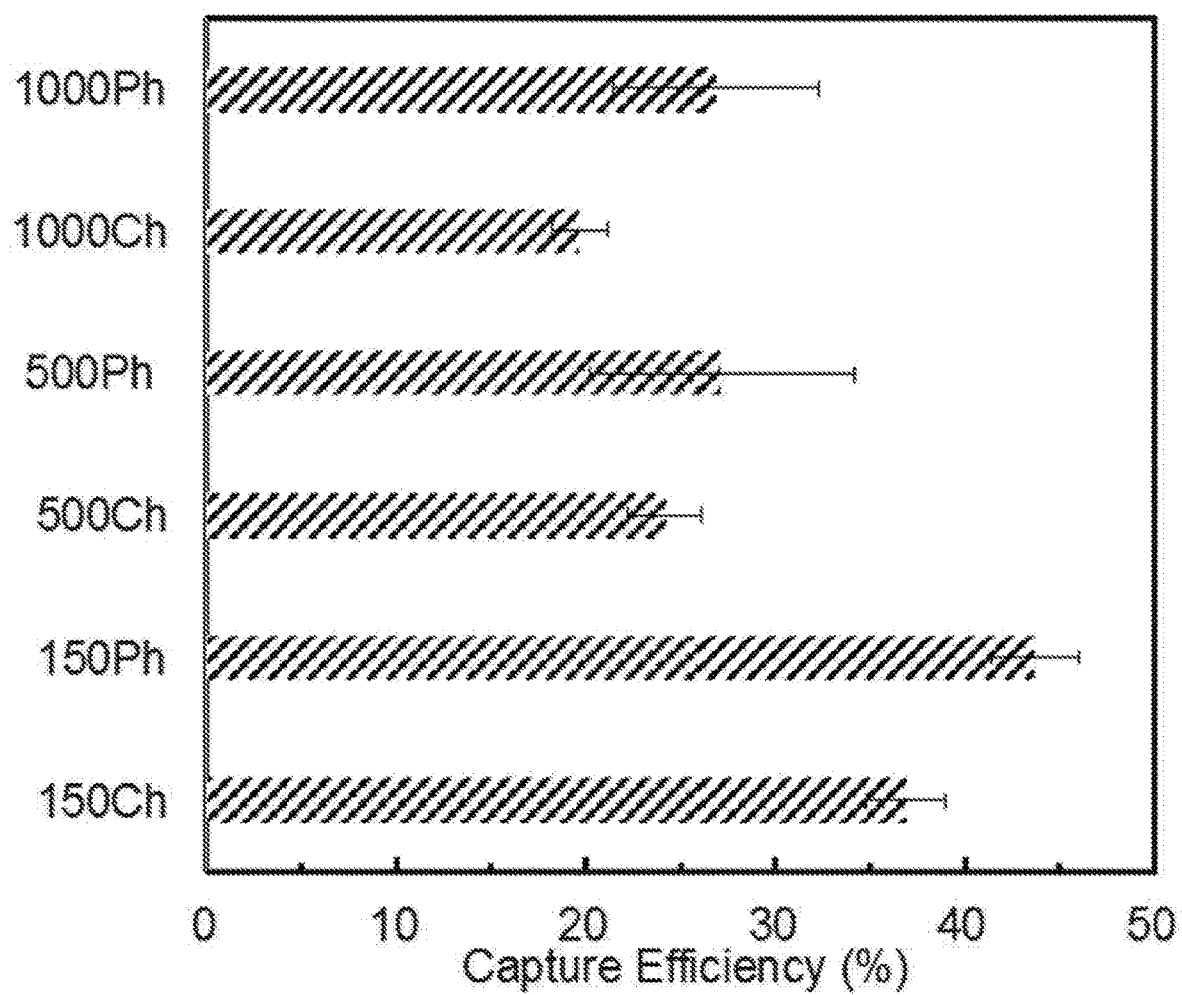
FIG. 14 graphs the capture efficiency of PMMP for the separation of *L. monocytogenes* from a suspension of $10^3$ CFU/mL.

In order to further understand influence of phage immobilization method and the corresponding PMMP effectiveness toward bacteria cell separation, experiments were conducted using PMMP prepared with $10^9$ PFU phages unless otherwise stated. Each PMMP (80 μL) was added into *L. monocytogenes* cell suspensions, and bacterial cells were isolated and separated using the method described in FIG. 13B. As a model system, *L. monocytogenes* at a concentration of $10^3$ CFU/mL was used for cell separation experiments, and the capture efficiency (CE) of each PMMP was evaluated and summarized in FIG. 14. As shown in FIG. 14, the capture efficiency of PMMP with chemically immobilized phages was lower than that of physically immobilized MP in all three sizes, which correlates with the observation about PMMP lytic activity. As mentioned previously, the low lytic activity of PMMP obtained using chemically immobilization may be due to the disorientation of phages on MP surface. These disoriented phages immobilized on PMMP may not be able to properly recognize and capture the host *L. monocytogenes* cells, leading to low bacterial capture efficiency.

PMMP with physically immobilized phages may contain higher numbers of "active" phage than that of PMMP with chemically immobilized phages. To evaluate the effect of the quantity of PMMP on *L. monocytogenes* capture efficiency, different volumes of 0.4 mg/mL PMMP (20 μL, 40 μL, 80 μL, 120 μL, 140 μL) of each size were added into 500 μL *L. monocytogenes* cell suspension of $10^3$ CFU/mL. As shown in Table 3.3, the CE of PMMP-150Ph increased from 23.9±6.0% to 54.7±0.86% with increasing PMMP dosage from 20 μL to 140 μL, which may be due to the availability of more surface-active sites for bacteria attachment. Similar trend was also observed for PMMP-150Ch, PMMP-500Ch, PMMP-500Ph, PMMP-1000Ch and PMMP-1000Ph.

TABLE 3.3

The effect of the MP quantity and immobilization method on the capture efficiency of bacteria cells using three sizes of MP (using $10^3$ CFU/mL *L. monocytogenes* as model analyte).

| | | % of captured bacteria cells ± SD | | | | | |
|---|---|---|---|---|---|---|---|
| | | 150Ch | 150Ph | 500Ch | 500Ph | 1000Ch | 1000Ph |
| Volume of MP | 20 | 13.9 ± 0.4 | 23.9 ± 6.0 | 15.0 ± 3.6 | 12.5 ± 2.2 | 10.5 ± 2.8 | 11.4 ± 5.3 |
| | 40 | 18.3 ± 5.3 | 34.6 ± 10.4 | 15.2 ± 2.2 | 21.2 ± 5.4 | 11.5 ± 3.1 | 18.4 ± 8.9 |
| | 80 | 37.0 ± 2.1 | 43.8 ± 2.3 | 24.2 ± 2.0 | 27.2 ± 7.0 | 19.7 ± 1.4 | 26.9 ± 5.4 |
| | 120 | 36.9 ± 5.0 | 58.0 ± 7.2 | 32.6 ± 7.1 | 41.1 ± 6.6 | 24.5 ± 5.0 | 40.9 ± 3.9 |
| | 140 | 39.3 ± 4.9 | 54.7 ± 0.86 | 38.5 ± 3.8 | 47.0 ± 0.5 | 28.4 ± 6.8 | 43.4 ± 0.4 |

Figure 15A:
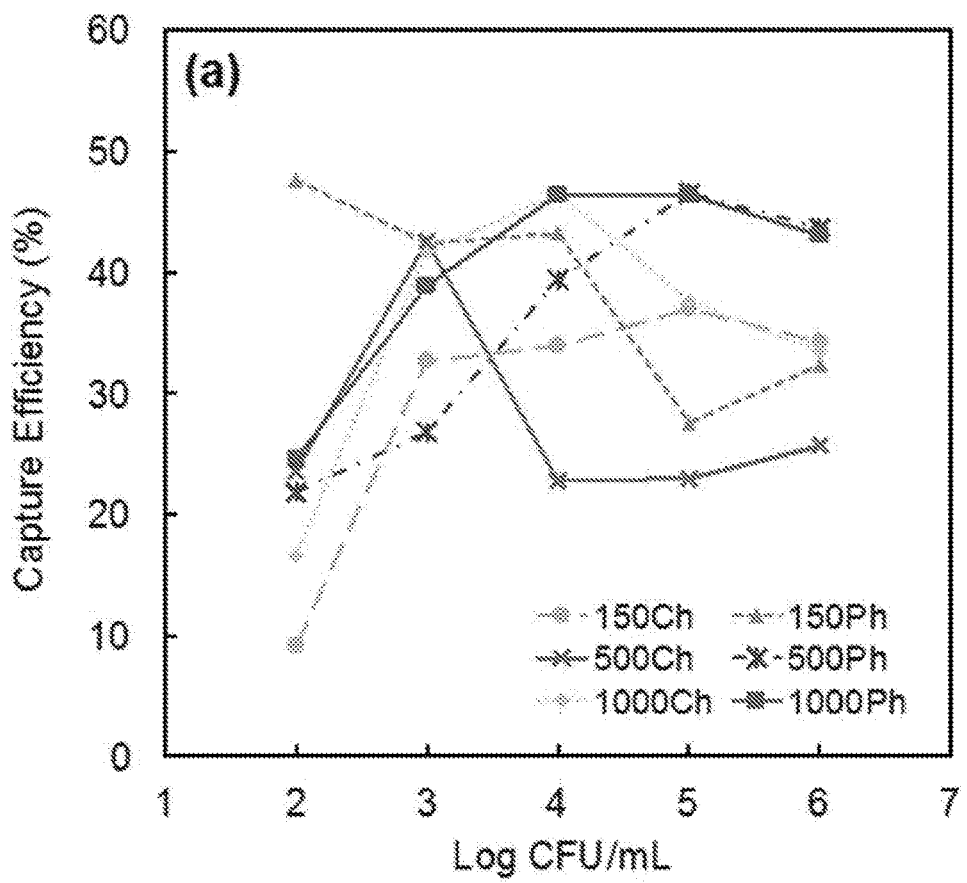
FIG. 15A plots the mean capture efficiency of phage-modified MP from cell suspension containing variable concentrations of *L. monocytogenes* ($10^2$-$10^6$ CFU/mL)
Figure 15B:
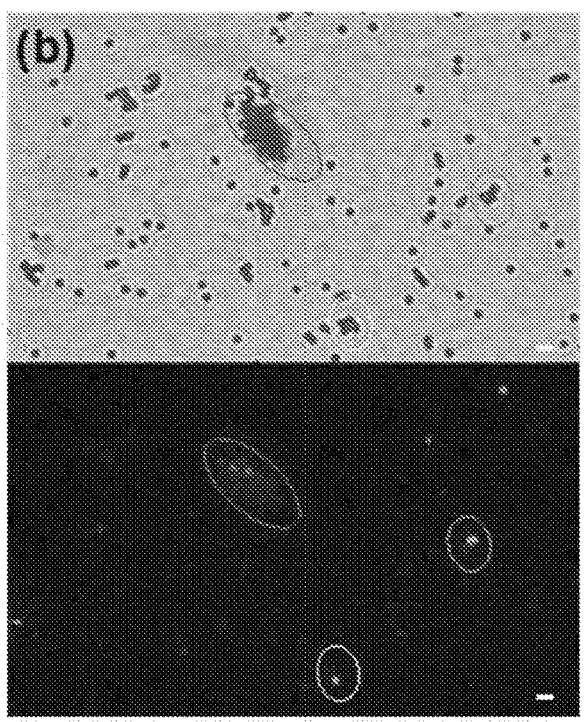
FIG. 15B provides images of transmitted (top) and fluorescence microscopy (bottom) images showing capture of bacteria using 1 μm MNP. Three spots were selected to show the captured bacteria on MP surfaces. The scale bar is 2 μm.
Figure 16:
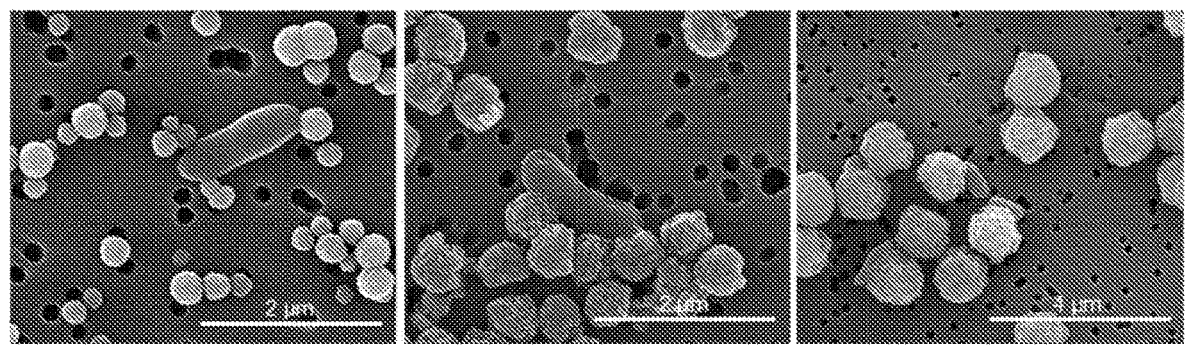
FIG. 16 shows SEM images of PMMP used for the capture of *L. monocytogenes*. (left 150 nm, middle 500 nm and right 1 μm MP).

In order to assess the capture efficiency of PMMP with varying numbers of *Listeria monocytogenes* cells ($10^2$-$10^6$ CFU/mL), 80 μL of each PMMP were added into respective cell suspensions containing *L. monocytogenes* cells, and the CE was calculated as mentioned previously. FIG. 15A shows the mean CE of PMMP from *L. monocytogenes* suspension. PMMP with physically immobilized phages showed higher CE than those with chemically immobilized phages. This effect was observed for all three sizes of PMMP. The CE of PMMP-150Ph at *L. monocytogenes* concentration of $10^2$ CFU/mL is 47%, which is higher than the CE of PMMP-150Ch particles (9%). Physical immobilization of phages likely favors the preferred orientation of phages to interact with bacteria cells, as reflected in the capture efficiency values. As shown in FIG. 15A, the CE at different *L. monocytogenes* concentrations showed that the highest capture efficiencies occur in the range of $10^3$ to $10^5$ CFU/mL for all particles studied. The lowest capture efficiencies for all particles were observed for $10^2$ CFU/mL. It was also noted that large MP showed higher CE at bacteria concentration above $10^4$ CFU/mL, whereas PMMP-150Ph showed the peak CE at low cell concentration ($10^2$ CFU/mL). The reduced performance of 150 nm PMMP for separation of high concentration of bacteria cell could be related to their particle aggregation, which reduces the number of particles that interact with bacteria cell. FIG. 15B shows the capture of fluorescence-labeled *L. monocytogenes* by PMMP-1000Ph magnetic particle on glass slide. The circled areas indicate the binding of bacterial cells on to PMMP, which confirms the successful separation of cells by PMMP-1000Ph from the cell suspension. The captured bacteria attached on PMMP were also observed in the SEM images shown in FIG. 16. Aggregation could be noticed in PMMP, and that the degree of aggregation is higher in small 150 nm MP, which may help explain the reduced lytic activity obtained by soft agar overlay.

Selectivity Test Using Other Bacterial Strains

Figure 17:
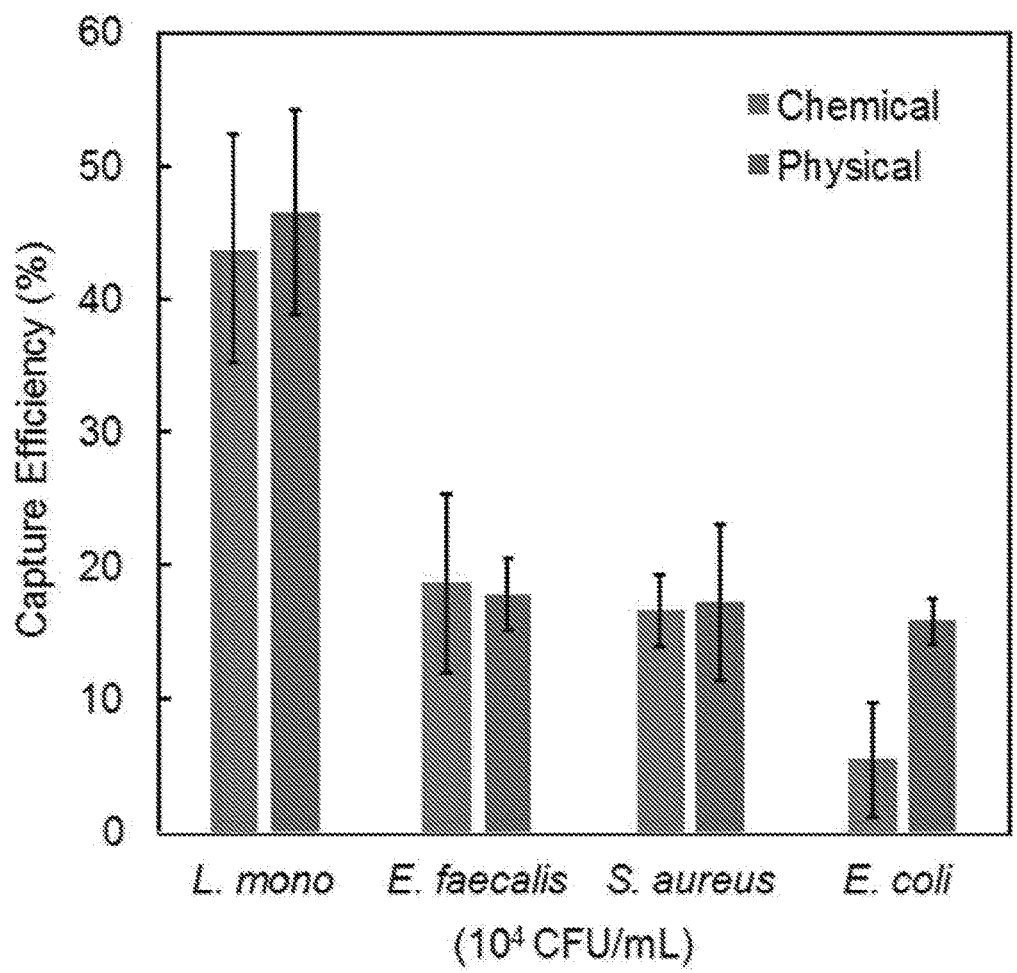
FIG. 17 provides results of a selectivity study of phage-modified 1 μm MP with selected bacteria strains. Red bar represents P100 chemically-immobilized MP; blue bar represents P100 physically-immobilized MP.

The selectivity of the PMMP based magnetic separation towards *L. monocytogenes* was evaluated using three other randomly selected strains of non-target bacteria namely *E. coli*, *S. aureus*, and *E. faecalis*. As shown in FIG. 17, the method achieved 40-50% CE of the target bacteria (*L. monocytogenes* Scott A), whereas the CE for non-target bacteria was only about 15%. The 15% capture of non-target cells could be due to the non-specific binding of bacteria cells on MP surface through FeO—P bonds between the bacterial cell membrane and the MP.[27,28]

Stability of PMMP

Figure 18:
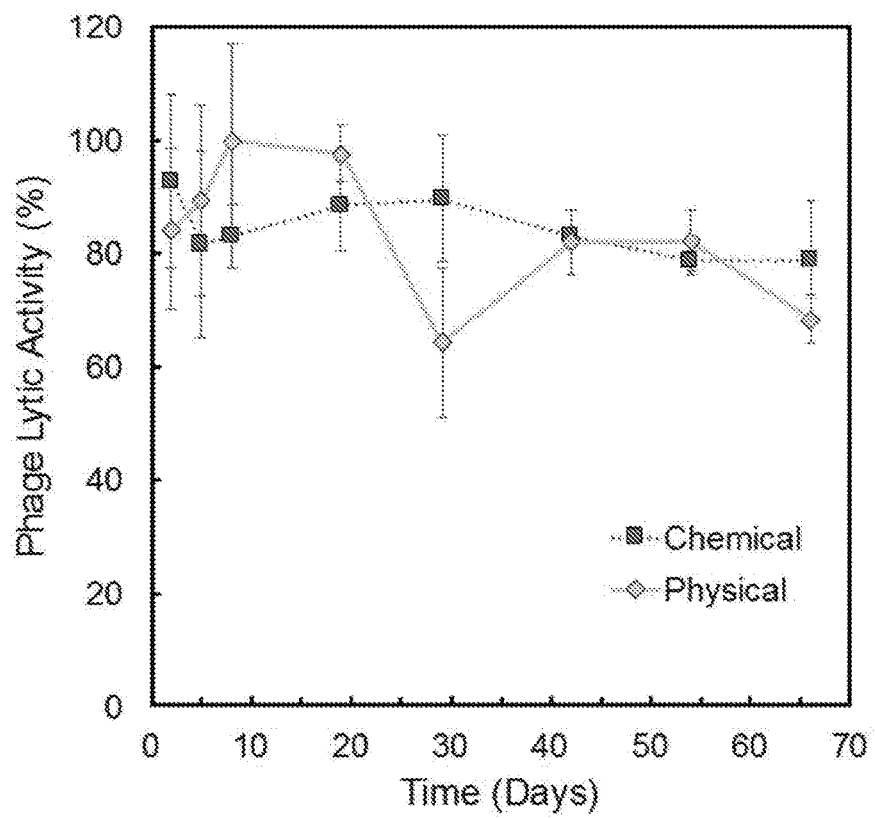
FIG. 18 illustrates the stability of physical/chemical functionalized magnetic particles. The blue dotted line represents the phage lytic activity of PMMP-1000Ch, and the yellow solid line represents the phage lytic activity of PMMP-1000Ph.

The stability of PMMP complexes was also studied by monitoring the immobilized phage activity using plaque assay. For this, PMMP were prepared using 1 μm magnetic particles via both physical and chemical immobilization methods. Plaque assay was performed using PMMP-1000Ch and PMMP-1000Ph for over 60 days. The PMMP lytic activity were obtained and compared to the first day lytic activity to evaluate their relative stability. FIG. 18 shows the relative PMMP lytic activity obtained from plaque assay in terms of PFU/mL. PMMP-1000Ch showed a quick drop in lytic activity after 5 days and retained steady lytic activity of about 78% after 66 days. On the other hand, the activity of PMMP-1000Ph fluctuated over a time range and remained 68% after 66 days. The prolonged stability of PMMP using chemical immobilization methods could be attributed to the strong covalent bonding between phages and MP, preventing phage desorption or disorientation, which may be the reason for the fluctuation of phage activity observed in physical immobilization method (as shown in FIG. 18). It was noted that the stability determination was based on relative activity of phages based on their activity on day 1 and therefore was not cross-compared between chemically and physically functionalized PMMP. Even though physical immobilization of phages likely favors the preferred orientation of phages, it is unclear if the resulting initial high lytic activity of physical immobilization will result in long-term retention of lytic activity of immobilized phages in PMMP.

Real Sample Testing

Figure 19:
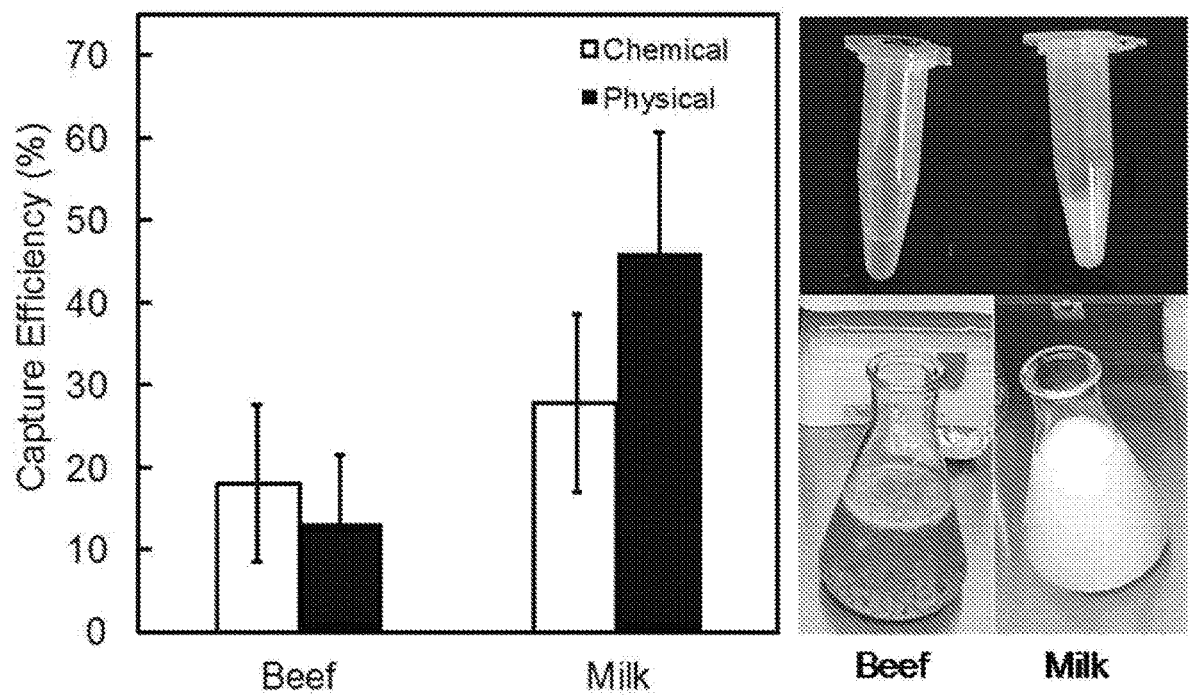
FIG. 19 illustrates separation of *L. monocytogenes* from pre-contaminated beef and milk samples ($10^3$ CFU/mL) using PMMP-1000Ch and PMMP-1000Ph.

The application of PMMP for *L. monocytogenes* isolation from whole milk and ground beef are presented in FIG. 19. Pre-contaminated milk and ground beef samples with $10^3$ CFU/mL of *L. monocytogenes* were used as real samples for magnetic separation. When PMMP-1000Ph and PMMP-1000Ch were used to capture $10^3$ CFUmL of *Listeria* in ground beef, the CE were 13% and 18%, respectively. Both PMMP-1000Ph and PMMP-1000Ch were then used to capture *Listeria* from milk, the CE were 46% and 28%, respectively. The results indicated that the CE obtained for separation of bacteria from ground beef was much lower than that from milk, and the CE values obtained using milk as food matrix were also close to CE obtained using PBS buffer as matrix. CE of *Listeria* cells were clearly influenced by different food matrix. A similar observation was reported for immuno-magnetic separation of *L. monocytogenes* cells from ground beef.[29] The low capture efficiency in ground beef may due to the greater solid and fat content in beef compared to milk, which may cause fouling and interference.

By chemical and physical immobilization method, P100 phages were immobilized onto three sizes of magnetic particles, which offered a useful label for rapid and specific separation of *Listeria monocytogenes*. The efficiency of bacterial capture by immobilized phage particles were influenced significantly by phage immobilization strategies and magnetic particle sizes. The resulting PMMP could effectively capture *L. monocytogenes* in food matrix. A comparison of the conventional methods (bacterial cell culture and IMS) with the presently described PMMP-assisted method for *L. monocytogenes* separation is given in Table 3.4. Based on microbiology and biochemical analysis, conventional culture methods are highly accurate but overly time-consuming that take up to 48 hours for separation and identification of *Listeria* cells. Moreover, an enrichment step is also required to grow the organisms, rendering it unsuitable for on-site separation and identification. IMS, on the other hand, has been widely used as an effective method for separation and isolation of *L. monocytogenes* from food, relying on the specificity of antibodies. Immunological based methods however suffer from harsh environmental conditions, high production cost of antibodies and the inconsistency in capture efficiency due to batch to batch variations. Unlike antibodies, bacteriophages are inexpensive to propagate and purify. PMMP obtained in this study could be used to separate *L. monocytogenes* cell within 20 minutes and cost about five dollars per sample. The achieved bacteriophage-assisted separation technique could also be applied for the separation of other bacteria strains from food matrix, representing an improved isolation/separation and concentration tool to the current standard method, IMS. Combination of this isolation and enrichment method with *Listeria* detection method including flow cytometry and biosensors, such as described in Example 1 and methods and systems of the present disclosure can reduce the assay time from 2-4 days to less than 20 min.

TABLE 3.4

Comparison of methods for *L. monocytogenes* separation.

| | Culture method [b] | IMS | PMMP |
|---|---|---|---|
| Time [a] | 18 h.-72 h. [30-32] | 30 min.~2 h. | 20 min. |
| % CE | N/A | 7%-121% [1,9,28,33-36] | 9-46% |
| Estimated cost/sample | ~$1 | ~$10-25 [30] | ~$4 |
| Labor | High | Medium | Medium |

[a] Approximate time it takes to perform the separation experiment.
[b] FDA-BAM was used as an example of culture method.

Example 3 References (1) Conrad, M. M. N. L.; Conceição, F. R.; Moreira, Â. N.; Silva, W. P. d.; Aleixo, J. A.; Bhunia, a. A. K. *BMC Microbiol.* 2012, 12.
(2) Välimaa, A.-L.; Tilsala-Timisjärvi, A.; Virtanen, E. *Food Control* 2015, 55, 103-114.
(3) Administration, U. S. F. a. D. Available at https://www.fda.gov/ICECI/ComplianceManuais/CompliancePolicyGuidanceManual/ucm136694.htm 2008.
(4) Oravcova, K.; Trncikova, T.; Kuchta, T.; Kaclikova, E. *J. Appl. Microbiol.* 2008, 104, 429-437.
(5) Martelet, A.; L'Hostis, G.; Nevers, M.-C.; Volland, H.; Junot, C.; Becher, F.; Muller, B. H. *Anal. Chem.* 2015, 87, 5553-5560.
(6) Suo, Z.; Yang, X.; Avci, R.; Deliorman, M.; Rugheimer, P.; Pascual, D. W.; Idzerda, Y. *Anal. Chem.* 2009, 81, 7571-7578.
(7) Xiong, Q.; Cui, X.; Saini, J. K.; Liu, D.; Shan, S.; Jin, Y.; Lai, W. *Food Control* 2014, 37, 41-45.
(8) Steingroewer, J.; Bley, T.; Bergemann, C.; Boschke, E. *J. Magn. Magn. Mater.* 2007, 311, 295-299.
(9) Yang, H.; Qu, L.; Wimbrow, A. N.; Jiang, X.; Sun, Y. *Int. J. Food Microbiol.* 2007, 118, 132-138.
(10) Koo, O. K.; Aroonnual, A.; Bhunia, A. K. *J. Appl. Microbiol.* 2011, 111, 93-104.
(11) Zhou, Y.; Marar, A.; Kner, P.; Ramasamy, R. P. *Anal. Chem.* 2017, 89, 5734-5741.
(12) Wang, Z.; Wang, D.; Chen, J.; Sela, D. A.; Nugen, S. R. *Analyst* 2016, 141, 1009-1016.
(13) Tolba, M.; Minikh, O.; Brovko, L. Y.; Evoy, S.; Griffiths, M. W. *Appl. Environ. Microbiol.* 2010, 76, 528-535.
(14) Hagens, S.; Loessner, M. J. *Front Microbiol* 2014, 5, 159.
(15) Smartt, A. E.; Xu, T.; Jegier, P.; Carswell, J. J.; Blount, S. A.; Sayler, G. S.; Ripp, S. *Anal. Bioanal. Chem.* 2012, 402, 3127-3146.
(16) Kanayeva, D. A.; Wang, R.; Rhoads, D.; Erf, G. F.; Slavik, M. F.; Tung, S.; Li, Y. *J. Food Prot.* 2012, 75, 1951-1959.
(17) U.S.D.A. Available at http://www.fda.gov/food/ingredientspackaginglabeling/gras/noticeinventory/ucm154675.htm 2006.
(18) U.S.D.A. pp. 47729-47732, 2006 Available at: http://edocket.access.gpo.gov2006/E6-13621.htm. 2006.
(19) U.S.D.A. Available at http://www.fda.gov/food/ingredientspackaginglabeling/gras/noticeinventory/ucm153865.htm 2007.
(20) Laube, T.; Cortés, P.; Llagostera, M.; Alegret, S.; Pividori, M. I. *Appl. Microbiol. Biotechnol.* 2014, 98, 1795-1805.
(21) Liebana, S.; Spricigo, D. A.; Cortes, M. P.; Barbe, J.; Llagostera, M.; Alegret, S.; Pividori, M. I. *Anal. Chem.* 2013, 85, 3079-3086.
(22) Zhan, S.; Yang, Y.; Shen, Z.; Shan, J.; Li, Y.; Yang, S.; Zhu, D. *J. Hazard. Mater.* 2014, 274, 115-123.
(23) Jin, Y.; Liu, F.; Shan, C.; Tong, M.; Hou, Y. *Water Res.* 2014, 50, 124-134.
(24) Chen, J.; Duncan, B.; Wang, Z.; Wang, L. S.; Rotelio, V. M.; Nugen, S. R. *Nanoscale* 2015, 7, 16230-16236.
(25) Singh, A.; Arutyunov, D.; Szymanski, C. M.; Evoy, S. *Analyst* 2012, 137, 3405-3421.
(26) Anany, R. C. H.; Gross, I.; Bhayani, R.; Griffiths, M.; Brook, M. A. *Biomaterials* 2010, 31, 1904-1910.
(27) Parikh, S. J.; Chorover, J. *Langmuir* 2006, 22, 8492-8500.
(28) Cagnasso, M.; Boero, V.; Franchini, M. A.; Chorover, J. *Colloids Surf. B. Biointerfaces* 2010, 76, 456-467.
(29) Shan, S.; Zhong, Z.; Lai, W.; Xiong, Y.; Cui, X.; Liu, D. *Food Control* 2014, 45, 138-142.
(30) Gasanov, U.; Hughes, D.; Hansbro, P. M. *FEMS Microbiol. Rev.* 2005, 29, 851-875.
(31) Law, J. W.; Ab Mutalib, N. S.; Chan, K. G.; Lee, L. H. *Front Microbiol* 2015, 6, 1227.
(32) Stevens, K. A.; Jaykus, L. A. *Crit. Rev. Microbiol.* 2004, 30, 7-24.
(33) Wadud, S.; Leon-Velarde, C. G.; Larson, N.; Odumeru, J. A. *J. Microbiol. Methods* 2010, 81, 153-159.
(34) Bilir Ormanci, F. S.; Erol, I.; Ayaz, N. D.; Iseri, O.; Sariguzel, D. *Br Pout Sci* 2008, 49, 560-565.
(35) Šafařík, I.; Šafaříková, M. *Journal of Chromatography B: Biomedical Sciences and Applications* 1999, 722, 33-53.
(36) Wang, H.; Li, Y.; Wang, A.; Slavik, M. *J. Food Prot.* 2011, 74, 2039-2047.

The invention claimed is:

1. A system for detecting bacteria in a sample, the method system comprising:
   magnetic particles functionalized with a first plurality of bacteriophages specific for a target strain of bacteria to be detected, wherein the bacteriophages are immobilized to the magnetic particle such that a majority of the phage are oriented in a head-in configuration relative to the magnetic particle such that a head of the bacteriophage is coupled to the magnetic particle and the tail of the bacteriophage is free to attach to bacterial cells of the target strain in a sample containing the target bacteria;
   a magnet configured to provide a magnetic field to the sample and to separate magnetic particle-coupled bacterial cells from other components in the sample to provide an enriched sample comprising a greater concentration of the target bacteria than the original sample;
   a bacteriophage-modified electrode comprising:
      an electrode material,
      a layer of multi-walled, carbon nanotubes (MWCNTs) on a surface of the electrode material thereby providing a MWCNT-modified electrode, wherein the MWCNT-modified electrode further comprises: an applied positive potential sufficient to provide a net positive surface charge to the MWCNT-modified electrode, and
      a second plurality of bacteriophages specific for the target strain of bacteria, the second plurality of bacteriophages immobilized to the MWCNTs via a linker, wherein the net positive surface charge of the MWCNT modified electrode is sufficient to facilitate charge-directed immobilization of the second plurality of bacteriophages such that the majority of the second plurality of bacteriophages on the electrode are oriented in a head-in, tail-out configuration relative to the electrode surface such that a head of the bacteriophage is coupled to the multi-walled, carbon nanotubes via the linker, wherein the second plurality of bacteriophages are capable of binding the target bacteria in the enriched sample; and a three-electrode electrochemical cell, in which the bacteriophage-modified electrode is a working electrode, wherein the system is configured to produce a detectable impedimetric signal upon binding of target bacteria to the phage-modified electrode.

2. The system of claim 1, wherein changes in the electrochemical parameters in the electrochemical cell are recorded as a cyclic voltammogram, differential pulse voltammogram, AC impedance, or other current response to an applied potential or voltage.

3. The system of claim 1, further comprising: a signal processing mechanism in operative communication with one or more elements of the electrochemical cell, the signal processing mechanism having data transfer and evaluation software protocols configured to transform raw data from the electrochemical cell into diagnostic information regarding the presence or absence of the target bacteria.

4. The system of claim 1, wherein the bacteriophages are non-covalently coupled to the magnetic particles.

5. The system of claim 1, wherein the magnetic particles are nanoparticles.

6. The system of claim 1, wherein the first plurality of bacteriophages are modified to comprise an affinity tag on a head of each bacteriophage, and wherein the magnetic particles are modified with a binding agent capable of binding to the affinity tag on the heads of the bacteriophages.

7. The system of claim 1, wherein the magnetic particle is from 50 nm to 5 μm.

8. A system for detecting bacteria in a sample, the method comprising:
  magnetic particles functionalized with a first plurality of bacteriophages specific for a target strain of bacteria to be detected, wherein the bacteriophages are immobilized to the magnetic particle such that a majority of the phage are oriented in a head-in configuration relative to the magnetic particle such that a head of the bacteriophage is coupled to the magnetic particle and the tail of the bacteriophage is free to attach to bacterial cells of the target strain in a sample containing the target bacteria;
  a magnet configured to provide a magnetic field to the sample and to separate magnetic particle-coupled bacterial cells from other components in the sample to provide an enriched sample comprising a greater concentration of the target bacteria than the original sample;
  a bacteriophage-modified electrode comprising:
    an electrode material,
    a layer of multi-walled, carbon nanotubes (MWCNTs) on a surface of the electrode material thereby providing a MWCNT-modified electrode, wherein the MWCNT-modified electrode further comprises: a cationic polymer and an applied positive potential, such that a combined positive charge from the cationic polymer and the applied positive potential provides a net positive surface charge, and
    a second plurality of bacteriophages specific for the target strain of bacteria, the second plurality of bacteriophages immobilized to the MWCNTs via a linker, wherein the net positive surface charge of the MWCNT modified electrode is sufficient to facilitate charge-directed immobilization of the second plurality of bacteriophages to the electrode surface via the linker in a head-in, tail out configuration relative to the electrode surface such that a head of the bacteriophage is coupled to the multi-walled, carbon nanotubes via the linker, wherein the second plurality of bacteriophages are capable of binding the target bacteria in the enriched sample; and
  a three-electrode electrochemical cell, in which the bacteriophage-modified electrode is a working electrode, wherein the system is configured to produce a detectable impedimetric signal upon binding of target bacteria to the phage-modified electrode.

9. A method of detecting bacteria in a sample, the method comprising:
  contacting a sample contaminated with a target strain of bacteria to the bacteriophage-functionalized magnetic particles of the system of claim 1, such that the bacteriophages bind to bacterial cells of the target strain in the sample thereby coupling the bacterial cells to the phage-functionalized magnetic particles;
  applying a magnetic field to the sample to separate magnetic particle-coupled bacterial cells from other components in the sample to provide an enriched sample comprising a greater concentration of the target bacteria than the original sample;
  contacting the enriched sample with a bacteriophage-modified electrode of the system of claim 1; and
  applying an electrical signal to the bacteriophage-modified electrode such that binding of the target bacteria to the phage-modified electrode produces a detectable impedimetric signal.

10. The method of claim 9, wherein the bacteria is foodborne pathogen, and wherein the sample is a food product.

11. The method of claim 9, wherein the magnetic particles are super paramagnetic nanoparticles (SPMNP).

12. The method of claim 9, wherein the bacteria is a strain selected from strains of *Escherichia coli*, *Listeria*, *Salmonella*, *Campylobacter*, *Vibrio vulnificus*, *Streptococcus*, Methicillin-resistant *Staphylococcus aureus* (MRSA) and *Mycobacterium bovis*.

13. The system of claim 1, wherein the bacteriophages are chemically crosslinked to the magnetic particles via a chemical linkage between each phage capsid and the surface of the magnetic particle, such that the majority of bacteriophages couple to the magnetic particle in a head-in, tail-out configuration.

14. The system of claim 1, wherein the bacteria is *Escherichia coli* B and the first plurality and the second plurality of bacteriophages are T2 phages.

15. The system of claim 1, wherein the bacteria is a strain of Escherichia coli O157 and the first plurality and the second plurality of bacteriophages are selected from the group of phages consisting of: PP01, e11/2, e4/1c, CEV1, and AR1.

16. The system of claim 1, wherein the bacteria is a strain of *Salmonella* and the first plurality and the second plurality of bacteriophages are selected from the group of phages consisting of: P22, SP6, ST104, and ST64T.

17. The system of claim 1, wherein the bacteria is a strain of *Listeria monocytogenes* and the first plurality and the second plurality of bacteriophages are selected from the group of phages consisting of: P100, A511, P35, A006, A500, and P35.

18. The system of claim 1, wherein the linker comprises pyrenebutanoic acid succinimidyl ester (PBSE) or a different molecule that comprises an aromatic ring on one side and a succimidyl ester on the other side.

19. The system of claim 1, wherein the MWCNT-modified electrode further comprises: a positively charged charge-modifying compound coupled to the MWCNTs to provide additional net positive surface charge to the MWCNT-modified electrode, such that the bacteriophages will orient in a head-in configuration to couple to the MWCNT.

20. The system of claim 19, wherein the charge-modifying compound coupled to the MWCNT is a cationic polymer having a positive charge, thereby conferring a positive surface charge to the MWCNT-modified electrode surface.

21. The system of claim 20, wherein the charge modifying compound comprises: polyethylenimine (PEI).

22. The system of claim 19, wherein the bacteriophage-modified electrode is made by the following steps:
   providing a MWCNT-modified electrode comprising a positively charged charge-modifying compound and the linker;
   applying a positive potential to the MWCNT-modified electrode; and
   providing the second plurality of bacteriophages, such that the positively charged charge-modifying compound and the applied positive potential provides a sufficient positive surface charge to facilitate charge-directed immobilization of the second plurality of bacteriophages to the electrode surface in a head-in, tail out configuration.

* * * * *